(12) United States Patent
Coulthard et al.

(10) Patent No.: US 10,016,539 B2
(45) Date of Patent: *Jul. 10, 2018

(54) MANUALLY POWERED, REGULATED, NEGATIVE PRESSURE PUMP WITH ADAPTER FOR EXTERNAL PRESSURE SOURCE

(71) Applicant: KCI Licensing, Inc., San Antonio, TX (US)

(72) Inventors: Richard Daniel John Coulthard, Verwood (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 1007 days.

This patent is subject to a terminal disclaimer.

(21) Appl. No.: 14/312,219

(22) Filed: Jun. 23, 2014

(65) Prior Publication Data
US 2015/0018784 A1 Jan. 15, 2015

Related U.S. Application Data

(60) Provisional application No. 61/844,743, filed on Jul. 10, 2013.

(51) Int. Cl.
*A61M 1/00* (2006.01)
*A61M 27/00* (2006.01)
(Continued)

(52) U.S. Cl.
CPC ........ *A61M 1/0035* (2014.02); *A61M 1/0031* (2013.01); *A61M 1/0068* (2014.02);
(Continued)

(58) Field of Classification Search
CPC ......... A61M 1/00; A61M 27/00; A61F 13/00; A61F 13/02; A61F 15/00
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986),pp. 94-96 (certified translation).
(Continued)

*Primary Examiner* — Tatyana Zalukaeva
*Assistant Examiner* — Ilya Treyger

(57) ABSTRACT

A manually-actuated pump for applying reduced-pressure therapy includes a charging chamber and a regulated chamber. The charging chamber has a closed end. A regulator passage extends between the charging chamber and the regulated chamber, and a valve body is adapted to control fluid communication through the regulator passage. A regulator spring is engaged with the valve body to bias the valve body against a differential between a pressure in the regulated chamber and an ambient pressure. The manually-actuated pump also includes an outlet port coupled to the regulated chamber; and a valve assembly coupled to the charging chamber to permit fluid flow through the closed end of the charging chamber.

37 Claims, 18 Drawing Sheets

(51) Int. Cl.
*A61F 13/00* (2006.01)
*A61F 13/02* (2006.01)
*A61F 15/00* (2006.01)

(52) U.S. Cl.
CPC ..... *A61M 1/0088* (2013.01); *A61M 2205/071* (2013.01); *A61M 2205/073* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,244,579 A * | 9/1993 | Horner ................ | B01D 61/022 210/195.2 |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,458,138 A * | 10/1995 | Gajo ................... | A61M 1/0001 128/205.12 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,174,306 B1 | 1/2001 | Fleischmann | |
| 6,241,747 B1 | 6/2001 | Ruff | |
| 6,261,276 B1 * | 7/2001 | Reitsma ............... | A61M 1/0023 604/319 |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| GB | 2465797 A | 6/2010 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | 2009/135171 A2 | 11/2009 |
| WO | 2011090996 A2 | 7/2011 |

(56) References Cited

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đ ukic, Ž. Maksimovic, Đ . Radek, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections form W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211).
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
Partial International Search Report for corresponding PCT/US2014/043719, dated Oct. 10, 2014.
Japanese Notice of Rejection for corresponding Application No. 2016525356, dated Mar. 27, 2018.

* cited by examiner

MANUALLY POWERED, REGULATED, NEGATIVE PRESSURE PUMP WITH ADAPTER FOR EXTERNAL PRESSURE SOURCE

RELATED APPLICATION

The present invention claims the benefit, under 35 USC § 119(e), of the filing of U.S. Provisional Patent Application Ser. No. 61/844,743, entitled "MANUALLY POWERED, REGULATED, NEGATIVE PRESSURE PUMP WITH ADAPTER FOR EXTERNAL PRESSURE SOURCE," filed Jul. 10, 2013, which is incorporated herein by reference for all purposes.

BACKGROUND OF THE INVENTION

Field of the Invention

The present invention relates generally to reduced pressure treatment systems and more particularly, but without limitation, to a manually-actuated reduced pressure treatment system having capabilities for providing a regulated pressure to a tissue site.

Description of Related Art

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure is commonly referred to as "reduced-pressure therapy," but may also be known by other names, including "negative pressure wound therapy" and "vacuum therapy," for example. Reduced-pressure therapy may provide a number of benefits, including migration of epithelial and subcutaneous tissues, improved blood flow, and microdeformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced pressure systems, components, and processes continues to present significant challenges to manufacturers, healthcare providers, and patients.

SUMMARY

The problems presented by existing reduced pressure systems are solved by the systems and methods of the exemplary embodiments described herein. In one exemplary embodiment, a manually-actuated pump for applying reduced-pressure therapy is described. The manually-actuated pump may include a charging chamber having a closed end, a regulated chamber, and a regulator passage between the charging chamber and the regulated chamber. The manually-actuated pump may also include a valve body adapted to control fluid communication through the regulator passage and a regulator spring engaged with the valve body to bias the valve body against a differential between a pressure in the regulated chamber and an ambient pressure. The manually-actuated pump may further include an outlet port coupled to the regulated chamber and a valve assembly coupled to the charging chamber to permit fluid flow through the closed end of the charging chamber.

In another embodiment, a reduced pressure treatment apparatus may be described. The reduced pressure treatment apparatus may include a piston chamber having a closed end, a piston disposed within the piston chamber and being movable between an extended position and a compressed position, and a charging chamber disposed between the piston and the closed end. A biasing member may be adapted to bias the piston toward the extended position, and a valve member may be adapted to allow fluid to exit the charging chamber as the piston moves toward the compressed position and to prevent fluid from entering the charging chamber as the piston moves toward the extended position. The apparatus may further include a regulated chamber, a passage between the regulated chamber and the charging chamber, and a regulator member to regulate fluid communication through the passage between the charging chamber and the regulated chamber. The apparatus may also include a valve assembly coupled to the charging chamber to permit fluid flow through the closed end of the charging chamber.

In still another embodiment, a reduced pressure treatment system is described. The reduced pressure treatment system may include a manifold adapted to be positioned at a tissue site. The system may further include a regulated chamber in fluid communication with the manifold and adapted to deliver a desired therapy pressure to the tissue site and a charging chamber having a closed end and adapted to store a charging pressure that is less than the desired therapy pressure. A passage may be adapted to provide fluid communication between the regulated chamber and the charging chamber. A valve body may be operably associated with the passage to substantially reduce fluid communication through the passage if a pressure in the regulated chamber is less than or equal to the desired therapy pressure and to allow fluid communication through the passage if the pressure in the regulated chamber exceeds the desired therapy pressure. A valve assembly may be coupled to the closed end of the charging chamber and adapted to be fluidly coupled to an external reduced-pressure source to permit fluid flow out of the charging chamber in response to a supplied pressure provided by the external reduced pressure source that is less than the pressure in the charging chamber.

In yet another embodiment, a method of providing reduced pressure treatment to a tissue site is described. A charging pressure may be stored within a charging chamber with an external reduced-pressure source. A desired therapy pressure may be delivered from a regulated chamber to the tissue site. If a pressure within the regulated chamber exceeds the desired therapy pressure, the pressure may be reduced within the regulated chamber by allowing fluid communication between the charging chamber and the regulated chamber.

Other objects, features, and advantages of the exemplary embodiments will become apparent with reference to the drawings and detailed description that follow.

DETAILED DESCRIPTION OF EXEMPLARY EMBODIMENTS

Figure 1:
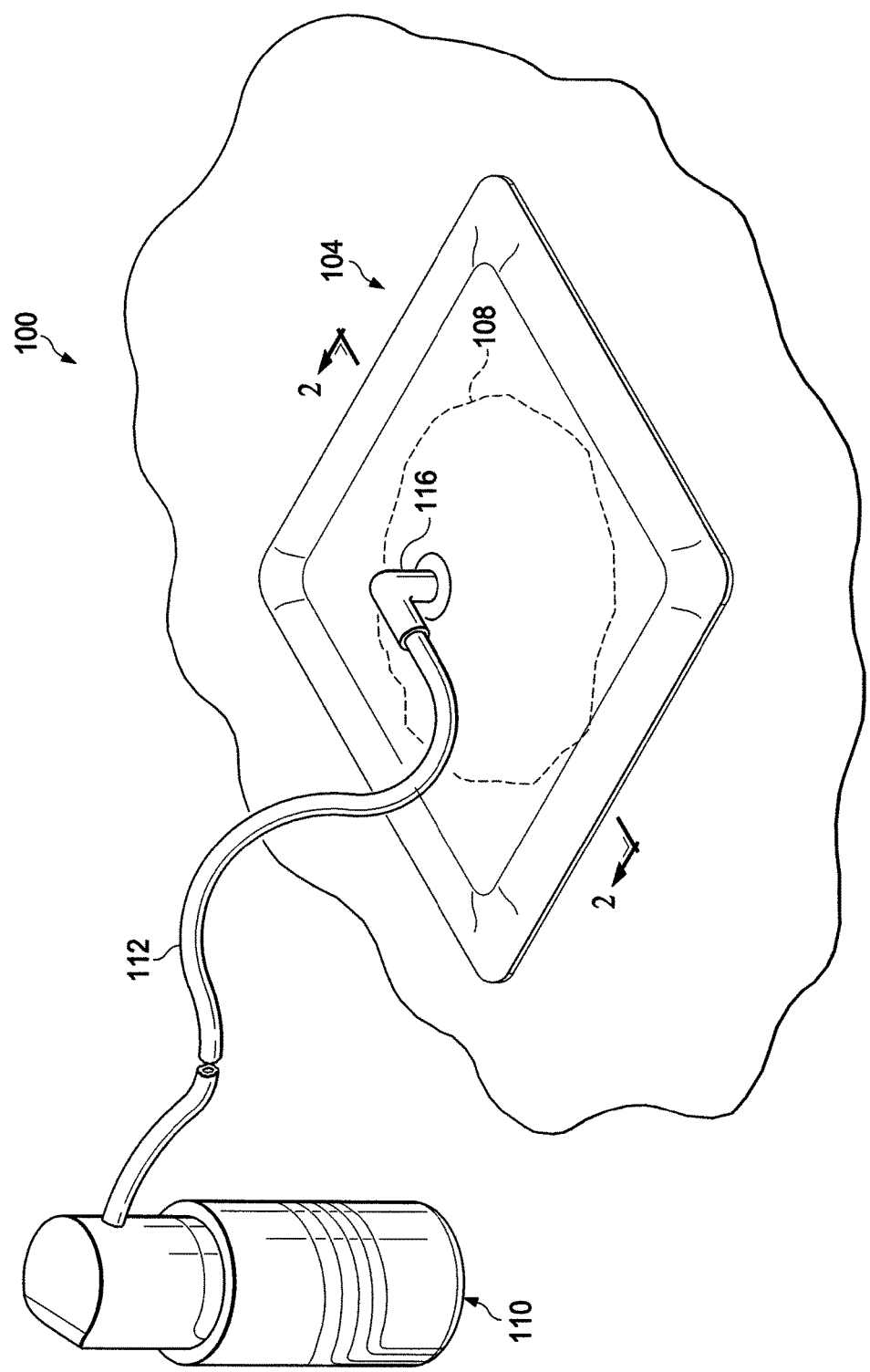
FIG. 1 is a perspective view of a reduced pressure treatment system according to an exemplary embodiment.

In the following detailed description of several exemplary embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the exemplary embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Reduced pressure treatment systems are often applied to large, highly exudating wounds present on patients undergoing acute or chronic care, as well as other severe wounds that are not readily susceptible to healing without application of reduced pressure. Low-severity wounds that are smaller and produce less exudate have generally been treated using advanced dressings instead of reduced pressure treatment. Improvements in wound healing, however, may be obtained by using reduced pressure treatment, even with smaller and less severe wounds.

Currently, the use of reduced pressure treatment is not considered a viable or affordable option for low-severity wounds due to the manpower required to monitor and change system components, the requirement for trained medical personnel overseeing treatment, and the cost of treatment. For example, the complexity of current reduced pressure treatment systems often limits the ability of a person with little or no specialized knowledge to administer such treatment to oneself or others. The size of current reduced pressure treatment systems can also impair the mobility of both the treatment system and the person to whom the treatment is being applied. For example, current reduced pressure treatment systems frequently require a separate canister that stores exudate or other liquid from the tissue site. Current reduced pressure treatment systems are also typically non-disposable after each treatment, and require electrical components or other powered devices in order to apply the reduced pressure used in treatment.

Eliminating power requirements can increase mobility and generally reduce cost. For example, a manually-actuated or manually-charged pump can be used as a source of reduced pressure instead of an electrically-powered pump. However, leaks in a dressing can gradually erode energy stored in the manually-actuated pump. Large leaks are also common when a dressing is first applied. A reduced-pressure therapy system using a manually-actuated pump can be particularly sensitive to leaks because the capacity of such a system to generate reduced pressure is typically more limited than systems using electrically-powered pumps. The presence of a leak at a dressing can quickly dissipate the therapeutic pressure generated by the manually-actuated pump.

A manually-actuated pump also works well for wound treatment where there is no hospital infrastructure accessible to the patient or a limited supply of medical equipment. However, where hospital infrastructure and medical equipment is available, having the patient charge or recharge a manually-actuated pump may be frustrating to the patient or the caregiver. Having a patient charge or recharge a manually-actuated pump may also be frustrating for a patient with an acute or low severity wound.

As described herein, a reduced pressure treatment system 100 can overcome these shortcomings and others by providing a manually-actuated pump that may be used to regulate reduced pressure supplied to the manually-actuated pump from external reduced-pressure sources, such as a conventional electric pump or a wall-suction source, for example. Referring to FIG. 1, a reduced pressure treatment system 100 according to an exemplary embodiment includes a reduced pressure dressing 104 positioned at a tissue site 108. The reduced pressure dressing 104 may be fluidly connected to a reduced-pressure source 110 by a conduit 112. The conduit 112 may fluidly communicate with the reduced pressure dressing 104 through a tubing adapter 116. In the exemplary embodiment of FIG. 1, the reduced-pressure source 110 is a manually-actuated pump. In other exemplary embodiments, the reduced-pressure source 110 may include pressure regulation capabilities and may initially be charged or re-charged to a selected reduced pressure by an external reduced-pressure source, such as an electrically driven pump or wall-suction source, for example. In still other embodiments, the reduced-pressure source 110 may be charged to the selected reduced pressure by a wall-suction source such as those available in hospitals and other medical facilities.

In general, components of the reduced-pressure therapy system 100 may be coupled directly or indirectly. For example, the reduced-pressure source 110 may be directly coupled to the conduit 112 and indirectly coupled to the reduced pressure dressing 104 through the conduit 112. In other embodiments, the reduced-pressure source 110 may be directly coupled to a canister (not shown) and indirectly coupled to the reduced pressure dressing 104 through the canister. Components may be fluidly coupled to each other to provide a path for transferring fluids (i.e., liquid and/or gas) between the components. In some embodiments, components may be fluidly coupled with a tube, such as the conduit 112, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

The reduced-pressure source 110 may be housed within or used in conjunction with a reduced pressure treatment unit (not shown), which may also contain sensors, processing units, alarm indicators, memory, databases, software, display units, and user interfaces that further facilitate the application of reduced pressure treatment to the tissue site 108. In one example, a sensor or switch (not shown) may be disposed at or near the reduced-pressure source 110 to determine a source pressure generated by the reduced-pressure source 110. The sensor may communicate with a processing unit that monitors and controls the reduced pressure that is delivered by the reduced-pressure source 110. Delivery of reduced pressure to the reduced pressure dressing 104 and the tissue site 108 encourages new tissue growth by maintaining drainage of exudate from the tissue site 108, increasing blood flow to tissues surrounding the tissue site 108, and creating microstrain at the tissue site 108.

Figure 2:
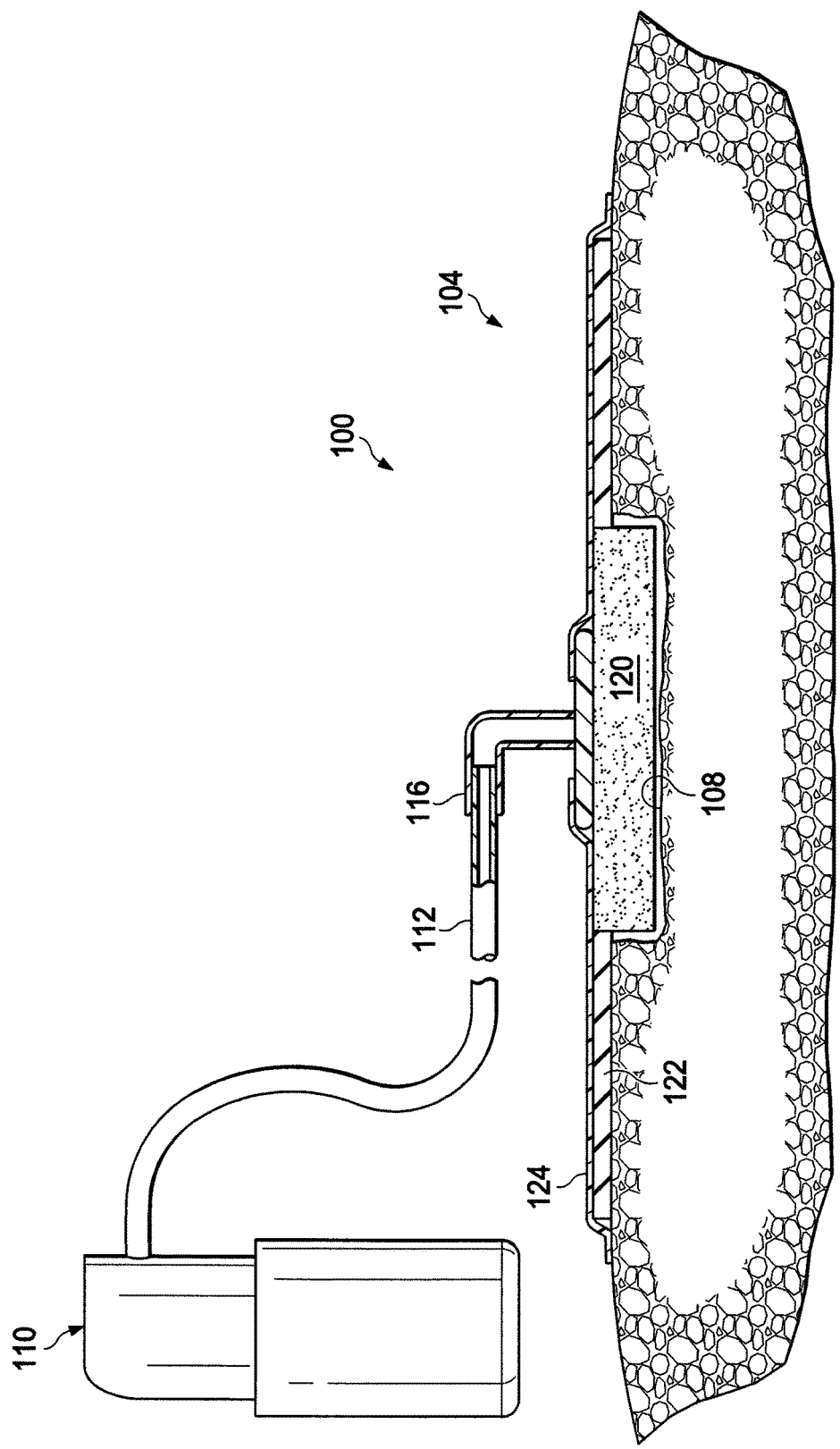
FIG. 2 is a cross-sectional front view of a dressing of FIG. 1 taken at line 2-2.

FIG. 2 is a sectional view, illustrating additional details of the reduced pressure dressing 104. The reduced pressure dressing 104 includes a distribution manifold 120 adapted to be positioned at the tissue site 108, and a seal layer 122 adapted to seal the reduced pressure dressing 104 to tissue proximate the tissue site 108. A cover 124 is positioned over the distribution manifold 120 and the seal layer 122 to maintain reduced pressure beneath the cover 124 at the tissue site 108. The cover 124 may extend beyond a perimeter of the tissue site 108 and may include an adhesive or bonding agent on the cover 124 to secure the cover 124 to tissue adjacent the tissue site 108. In some embodiments, the adhesive disposed on the cover 124 may be used in lieu of the seal layer 122. In other embodiments, the seal layer 122 may be used in conjunction with the adhesive of the cover 124 to improve sealing of the cover 124 at the tissue site 108. In another embodiment, the seal layer 122 may be used in lieu of adhesive disposed on the cover 124.

The cover 124 is an example of a sealing member and may also be referred to as a drape. A sealing member may be constructed from a material that can provide a fluid seal between two components or two environments, such as between a therapeutic environment and a local external environment. A sealing member may be, for example, an impermeable or semi-permeable, elastomeric material that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery of, a portion of, or an entire sealing member. Other example embodiments of an attachment device may include a double-sided tape, paste, hydrocolloid, hydrogel, silicone gel, organogel, or an acrylic adhesive.

The distribution manifold 120 can be generally adapted to contact a tissue site. The distribution manifold 120 may be partially or fully in contact with the tissue site. If the tissue site is a wound, for example, the distribution manifold 120 may partially or completely fill the wound, or may be placed over the wound. Although the distribution manifold 120 illustrated in FIG. 2 has a rectangular cross-section, the distribution manifold 120 may take many forms, and may have many sizes, shapes, or thicknesses depending on a variety of factors, such as the type of treatment being implemented or the nature and size of a tissue site. For example, the size and shape of the distribution manifold 120 may be adapted to the contours of deep and irregular shaped tissue sites.

More generally, a manifold is a substance or structure adapted to distribute reduced pressure to a tissue site, remove fluids from a tissue site, or both. In some embodiments, though, a manifold may also facilitate delivering fluids to a tissue site, if the fluid path is reversed or a secondary fluid path is provided, for example. A manifold may include flow channels or pathways that distribute fluids provided to and removed from a tissue site around the manifold. In one exemplary embodiment, the flow channels or pathways may be interconnected to improve distribution of fluids provided to or removed from a tissue site. For example, cellular foam, open-cell foam, porous tissue collections, and other porous material such as gauze or felted mat generally include structural elements arranged to form flow channels. Liquids, gels, and other foams may also include or be cured to include flow channels.

In one exemplary embodiment, the distribution manifold 120 may be a porous foam material having interconnected cells or pores adapted to uniformly (or quasi-uniformly) distribute reduced pressure to a tissue site. The foam material may be either hydrophobic or hydrophilic. In one non-limiting example, the distribution manifold 120 can be an open-cell, reticulated polyurethane foam such as Granu-Foam® dressing available from Kinetic Concepts, Inc. of San Antonio, Tex.

In an example in which the distribution manifold 120 may be made from a hydrophilic material, the distribution manifold 120 may also wick fluid away from a tissue site while continuing to distribute reduced pressure to the tissue site. The wicking properties of the distribution manifold 120 may draw fluid away from a tissue site by capillary flow or other wicking mechanisms. An example of a hydrophilic foam is a polyvinyl alcohol, open-cell foam such as V.A.C. White-Foam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The distribution manifold 120 may further promote granulation at the tissue site 108 if a reduced pressure is applied through the reduced pressure dressing 104. For example, any or all of the surfaces of the distribution manifold 120 may have an uneven, coarse, or jagged profile that causes microstrains and stresses at the tissue site 108 if reduced pressure is applied through the distribution manifold 120. These microstrains and stresses have been shown to increase new tissue growth.

In some embodiments, the distribution manifold 120 may be constructed from bioresorbable materials that do not have to be removed from a patient's body following use of the reduced pressure dressing 104. Suitable bioresorbable materials may include, without limitation, a polymeric blend of polylactic acid (PLA) and polyglycolic acid (PGA). The polymeric blend may also include without limitation polycarbonates, polyfumarates, and capralactones. The distribution manifold 120 may further serve as a scaffold for new cell-growth, or a scaffold material may be used in conjunction with the distribution manifold 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Figure 3:
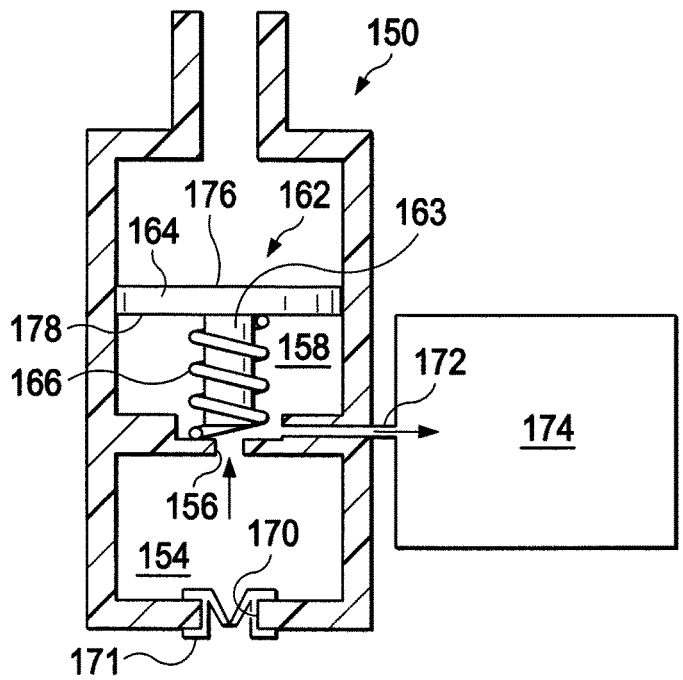
FIG. 3 is a schematic view of a reduced pressure treatment apparatus shown in a first position according to an exemplary embodiment.
Figure 4:
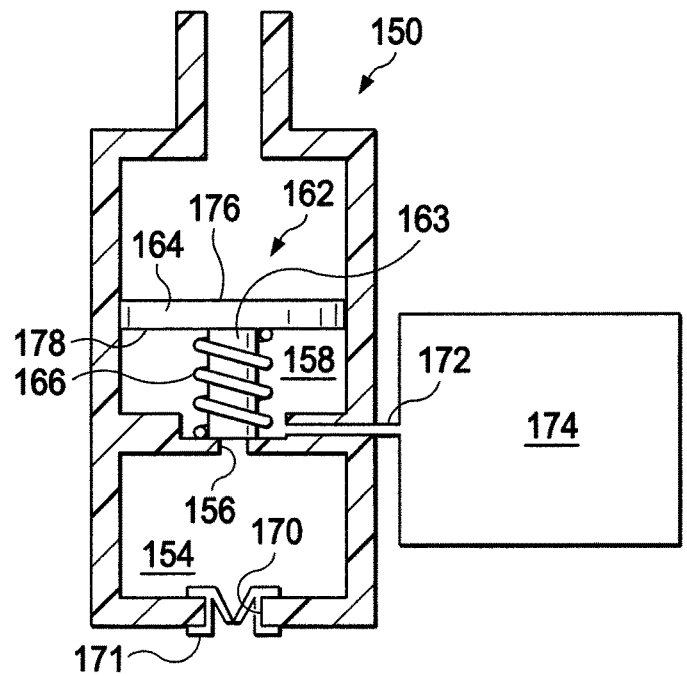
FIG. 4 is a schematic view of the reduced pressure treatment apparatus of FIG. 3 in a second position.

FIG. 3 is a sectional view, illustrating additional details of a reduced pressure treatment apparatus 150, which may also be referred to as a reduced pressure pump or a reduced-pressure source. The reduced pressure treatment apparatus 150 includes a charging chamber 154 fluidly connected by a conduit, such as a passage 156, to a regulated chamber 158. A regulator member 162 can be operably associated with the passage 156 to selectively allow or prevent fluid communication between the charging chamber 154 and the regulated chamber 158. In some embodiments, the regulator member 162 includes a piston 164 that is disposed within the regulated chamber 158. The piston 164 may include a valve body 163. The regulator member 162 further includes a regulator spring 166 to bias the piston 164 toward an open position as illustrated in FIG. 3. In the open position, the piston 164 and the valve body 163 allow fluid communication through the passage 156. FIG. 4 is a sectional view, illustrating additional details of the reduced pressure treatment apparatus 150 in a closed position. In the closed position, the piston 164 and the valve body 163 prevent or at least substantially reduce fluid communication through the passage 156.

As previously noted, the charging chamber 154 may be fluidly connected to the regulated chamber 158 by the passage 156. The charging chamber 154 may include an inlet 170 for introduction of a reduced pressure to the charging chamber 154. In some embodiments, the charging chamber 154 may be operably associated with a piston-driven or other device to charge the charging chamber 154 with the reduced pressure. Charging the charging chamber 154 may also be referred to as priming the charging chamber 154. Charging or priming the reduced pressure treatment apparatus 150 may refer to supplying the charging chamber 154 with a reduced pressure for operation of the reduced pressure treatment apparatus 150. In some embodiments, charging or priming the reduced pressure treatment apparatus 150 may include reducing pressure in the charging chamber 154. The supplied pressure may be a pressure that is less than an ambient or atmospheric pressure and that may be provided to the reduced pressure treatment apparatus 150 and the charging chamber 154 from an external reduced pressure source. The charging chamber 154 is well suited to receive the reduced pressure or supplied pressure from a device that is manually-actuated, or alternatively that is powered by electrical or other means.

In some embodiments, a check valve 171 may be positioned in the inlet 170. The check valve 171 may be a duckbill valve, an umbrella valve, or a sprung-ball valve, for example. The check valve 171 may be sized to couple to the inlet 170 in an interference fit so that fluid communication through the inlet 170 may occur through a valve passage of the check valve 171. In other embodiments, the check valve 171 may be coupled with fasteners, by welding, or with adhesives, for example. The check valve 171 may be oriented to permit fluid communication from the charging chamber 154 through the check valve 171 into the ambient environment and prevent fluid communication from the ambient environment through the check valve 171 into the charging chamber 154.

The regulated chamber 158 can be fluidly connected by a conduit 172 to a dressing 174. In some embodiments, the conduit 172 and the dressing 174 may be similar or analogous to the conduit 112 and the dressing 104. If reduced pressure treatment is applied to the dressing 174 and a tissue site, it is preferred to deliver a reduced pressure to the dressing 174 that is about equal to a desired therapy pressure. To accomplish this, the charging chamber 154 can store a first pressure that is less than an ambient pressure, and the regulated chamber 158 can store a second pressure that is also less than the ambient pressure. The first pressure stored in the charging chamber 154 may be less than the second pressure stored in the regulated chamber 158.

If the second pressure in the regulated chamber 158 is less than or equal to the desired therapy pressure, a counteracting force on the piston 164 is able to overcome a biasing force exerted by the regulator spring 166 on the piston 164. The counteracting force on the piston 164 is a result of a pressure differential across the piston 164. On a first side 176 of the piston 164, the ambient pressure (e.g. atmospheric pressure) surrounding the reduced pressure treatment apparatus 150 acts on the piston 164. On a second side 178 of the piston 164, the second pressure within the regulated chamber 158 acts on the piston 164. Since the second pressure is less than the ambient pressure, the counteracting force acts on the first side 176 of the piston 164 against the biasing force of the regulator spring 166. If the second pressure in the regulated chamber 158 is less than or equal to the desired therapy pressure, the piston 164 moves the valve body 163 to the closed position as shown in FIG. 4 so that the valve body 163 may block the passage 156.

If the second pressure in the regulated chamber 158 rises above (i.e. exceeds) the desired therapy pressure, possibly due to fluid leaks at the dressing 174 or within the reduced pressure treatment apparatus 150, the piston 164 is biased back to the open position by the regulator spring 166 as shown in FIG. 3. In the open position, fluid communication is allowed between the charging chamber 154 and the regulated chamber 158 through the passage 156. Since the first pressure in the charging chamber 154 is less than the second pressure in the regulated chamber 158, the second pressure in the regulated chamber 158 drops until the desired therapy pressure is reached, at which point the piston 164 again moves the valve body 163 to the closed position as shown in FIG. 4.

If a dressing, such as the dressing 174, has a small leak, the regulator member 162 can maintain the therapy pressure. However, the regulator member 162 may not be able to maintain the therapy pressure if a leak exceeds a certain tolerance. The leak tolerance may be dependent upon the size of the restrictions on the entry and exit sides of the regulated chamber 158. For example, the passage 156 and the conduit 172 may be sized such that a leak exceeding a threshold causes the regulator member 162 to remain partially open, creating a gap between the regulator member 162 and the passage 156 that allows a steady flow of air through the passage 156 and the conduit 172. Moreover, the sizes of the passage 156 and the conduit 172 may be calibrated such that the flow of air through the gap causes an audible note, alerting an operator of an unexpected loss of therapeutic pressure.

In some embodiments, the first pressure stored in the charging chamber 154 is about −150 mm Hg, and the desired therapy pressure is about −125 mm Hg. At initial operation, the first pressure may be greater than −150 mm Hg. In some embodiments, an external reduced-pressure source, such as an electrically operated vacuum or a wall-suction source, for example, may be fluidly coupled to the charging chamber 154. Activation of the external reduced-pressure source may generate a third pressure adjacent the inlet 170 and the check valve 171 that is less than the first pressure in the charging chamber 154. If the third pressure is less than the first pressure, the check valve 171 will open and at least partially evacuate the charging chamber 154 through the check valve 171. The at least partial evacuation of the charging chamber 154 lowers the first pressure until the first pressure is approximately equal to the third pressure, thereby charging the reduced pressure treatment apparatus 150 for application of reduced-pressure therapy. The piston 164 and the regulator spring 166 may operate as described above to provide the therapy pressure to the dressing 174.

Once the therapy pressure is reached at the dressing 174, the piston 164 may operate as described above to close the passage 156. In an exemplary embodiment, the external reduced-pressure source may remain fluidly coupled to the reduced pressure treatment apparatus 150. The external reduced-pressure source may maintain the first pressure in the charging chamber 154 within a predetermined tolerance of the third pressure supplied by the external reduced-pressure source through the check valve 171 and the inlet 170.

In another exemplary embodiment, the external reduced-pressure source may be uncoupled from the reduced pressure treatment apparatus 150. If the external reduced-pressure source is uncoupled from the reduced pressure treatment apparatus 150, the pressure external to the charging chamber 154 adjacent the inlet 170 and the check valve 171 may return to the ambient pressure (i.e. atmospheric pressure), which may be greater than the first pressure in the charging chamber 154. If the ambient pressure adjacent the outlet 170 and the check valve 171 external to the charging chamber 154 is greater than the first pressure, the check valve 171 may close, preventing the equalization of the first pressure with the ambient pressure through the inlet 170 and the check valve 171.

By permitting the evacuation of the charging chamber 154 and preventing the equalization of the first pressure in the charging chamber 154 with an ambient pressure, the check valve 171 allows the reduced pressure treatment apparatus 150 to be selectively charged through the inlet 170. Selective charging permits the reduced pressure treatment apparatus 150 to be used in conjunction with medical equipment available in an environment having hospital infrastructure. For example, reduced-pressure therapy may begin with the reduced pressure treatment apparatus 150 at a hospital by coupling a wall-suction source to the reduced pressure treatment apparatus 150 and regulating reduced pressure to the dressing 174. Once the therapy pressure is reached at the dressing 174, the wall-suction source may be uncoupled from the reduced pressure treatment apparatus 150, permitting the patient to be ambulatory while still receiving the reduced-pressure therapy.

Figure 5:
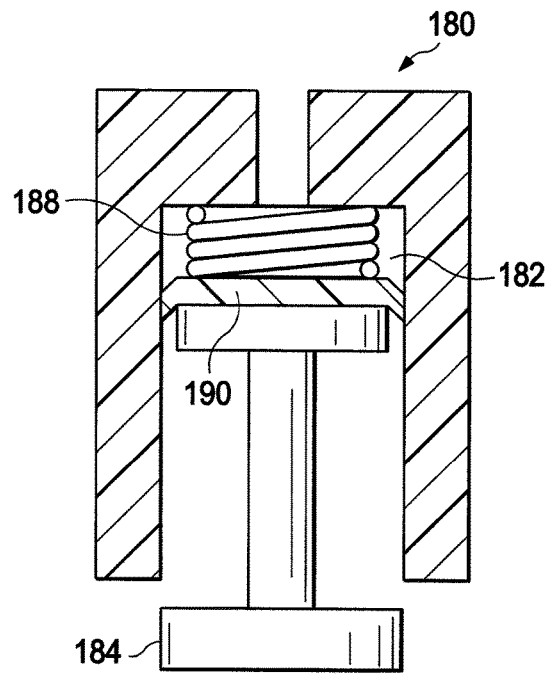
FIG. 5 is a schematic view of a piston-driven device in a first position for use with the reduced pressure treatment apparatus of FIG. 3.
Figure 6:
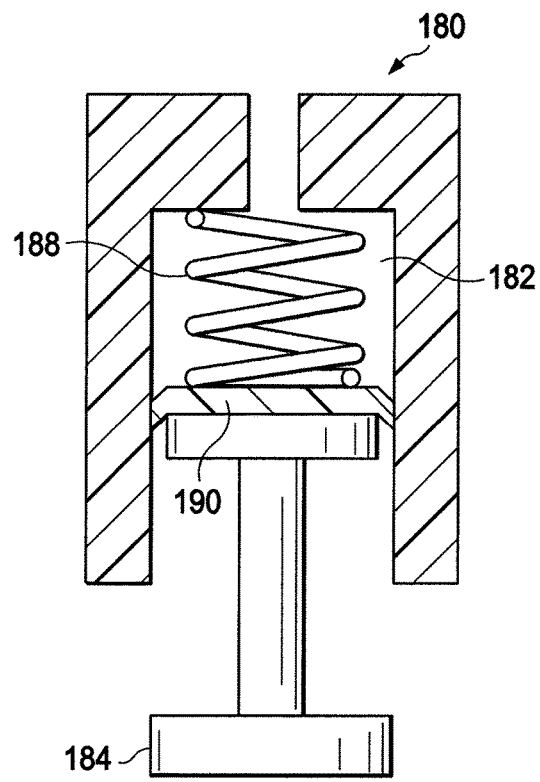
FIG. 6 is a schematic view of the piston-driven device of FIG. 5 in a second position.

FIG. 5 and FIG. 6 are sectional views illustrating additional details of a piston-driven device 180. The piston driven device 180 is an example of a device that may be provided for charging a charging chamber 182 similar or analogous to the charging chamber 154 of FIGS. 3 and 4. As illustrated in FIGS. 5 and 6, the piston-driven device 180 includes a piston 184 disposed within the charging chamber 182. This piston 184 is capable of reciprocal movement between a compressed position, as shown in FIG. 5, and an expanded position, as shown in FIG. 6. A piston spring 188 or other biasing member may be operably associated within the piston 184 to bias the piston 184 toward the expanded position.

To charge the charging chamber 182, the piston 184 can be moved to the compressed position. A seal 190 or other valve member allows fluid within the charging chamber 182 to exit the charging chamber 182 as a volume of the charging chamber 182 decreases. After moving the piston 184 to the compressed position, the piston spring 188 applies a force on the piston 184, which motivates the piston 184 to the expanded position. As the volume of the charging chamber 182 increases, the seal 190 prevents fluid from entering the charging chamber 182 past the seal 190, which results in a reduced pressure within the charging chamber 182. After the piston 184 has moved completely to the extended position, the piston 184 may be moved again to the compressed position to recharge the charging chamber 182 with a reduced pressure.

The piston-driven device 180 may be manually-actuated by a user compressing the piston 184. Alternatively, the piston 184 may be actuated by an electrical, hydraulic, or pneumatic actuator. For all of the charging chambers described herein, it should be noted that reduced pressure may be supplied to the charging chamber by manual or electrically powered means.

Figure 7:
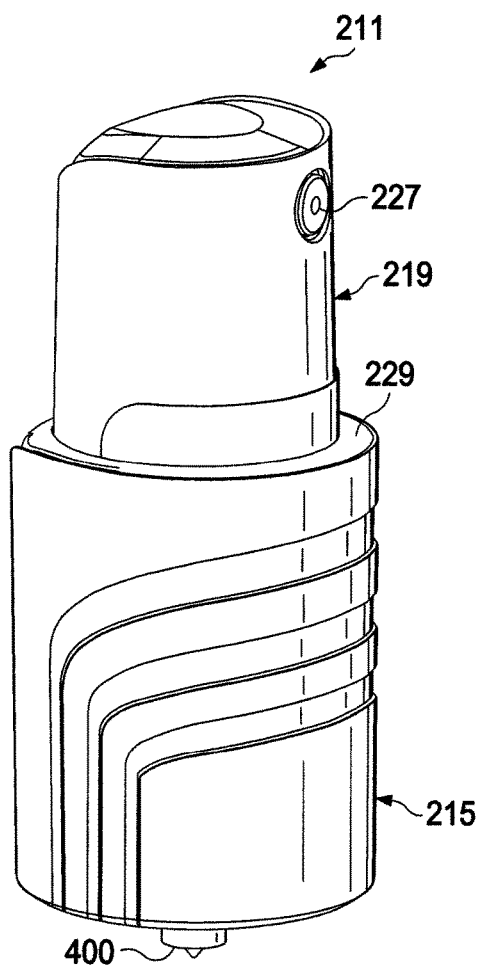
FIG. 7 is a side perspective view of a reduced pressure treatment apparatus according to an exemplary embodiment.
Figure 8:
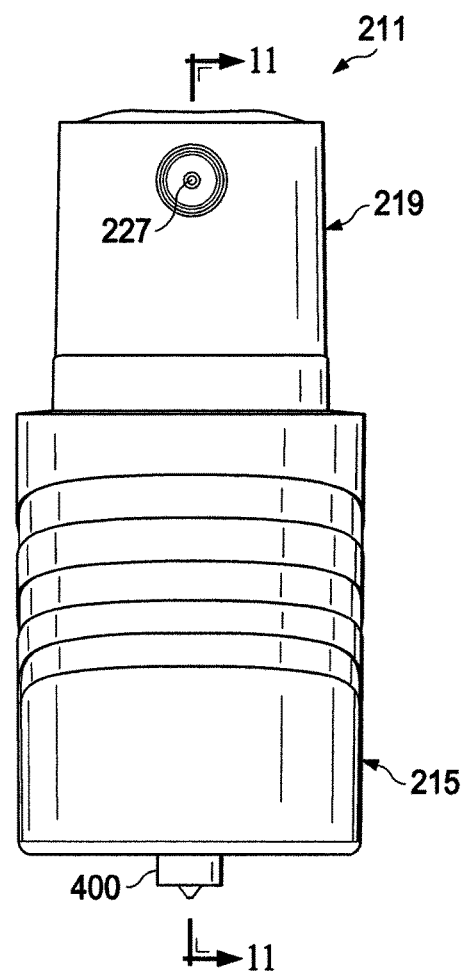
FIG. 8 is a front view of the reduced pressure treatment apparatus of FIG. 7.

FIG. 7 is a perspective view and FIG. 8 is a front elevation view, illustrating additional details of a reduced-pressure source 211. The reduced-pressure source 211 may also be referred to as a reduced pressure treatment apparatus, a manually-actuated pump, or a pump. The reduced-pressure source 211 may have an outer barrel, such as a first barrel 215, and an inner barrel, such as a second barrel 219. While the first barrel 215 and the second barrel 219 are illustrated as having substantially cylindrical shapes, the shapes of the first barrel 215 and the second barrel 219 could be other shapes that permit operation of the device. An outlet port 227 may be provided on the second barrel 219 and may be adapted for fluid communication with a delivery tube or other conduit, which may be similar to the conduit 112, such that reduced pressure generated by the reduced-pressure source 211 may be delivered to the tissue site, such as the tissue site 108. The reduced-pressure source 211 may further include a barrel ring 229. The barrel ring 229 can be positioned at an open end of the first barrel 215 to circumscribe the second barrel 219. The barrel ring 229 can eliminate gaps between the first barrel 215 and the second barrel 219 at the open end of the first barrel 215. A valve assembly 400 may be coupled to the first barrel 215 opposite the second barrel 219.

Figure 9:
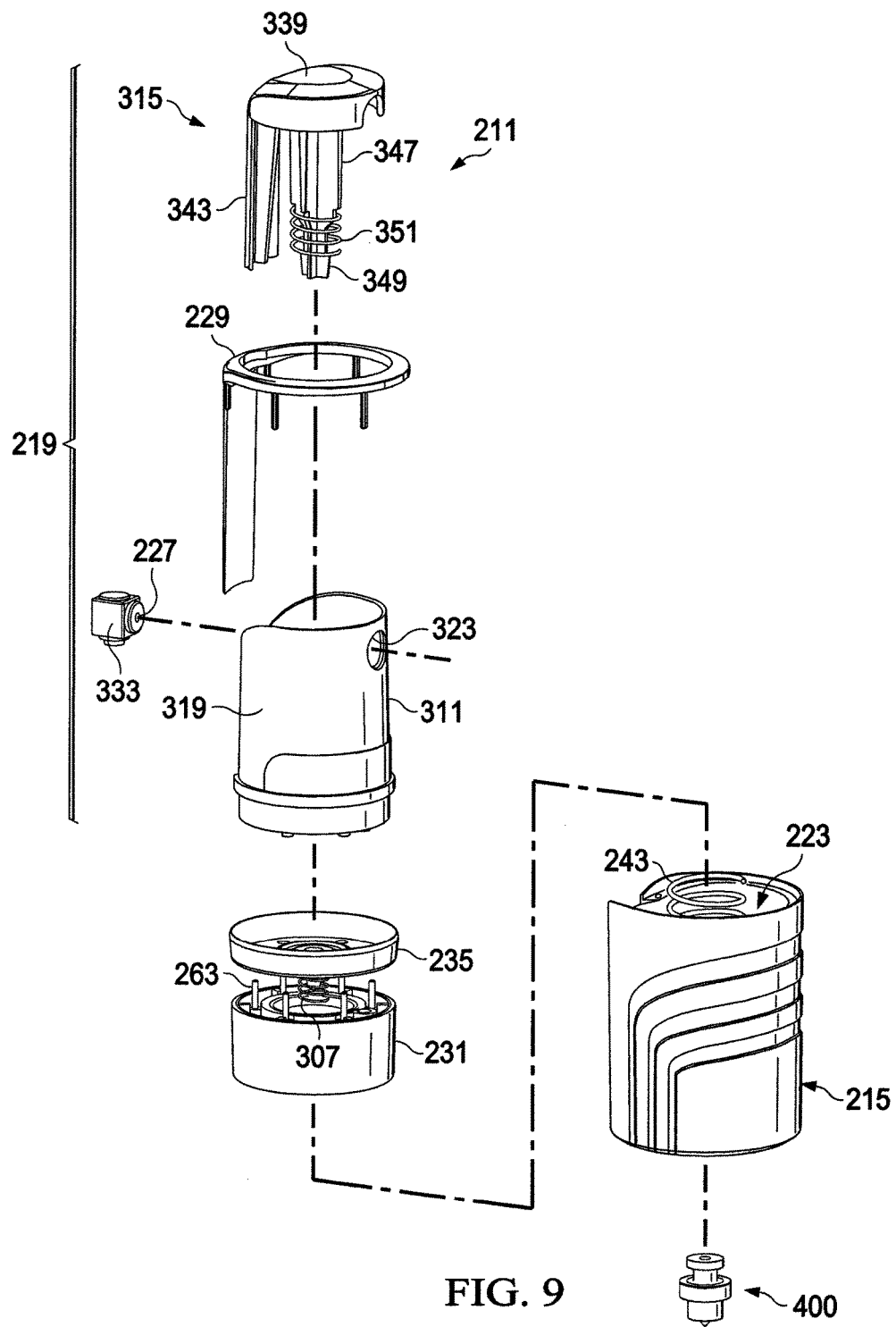
FIG. 9 is an exploded side perspective view of the reduced pressure treatment apparatus of FIG. 7.

FIG. 9 is an exploded view, illustrating additional details of the reduced-pressure source 211. As shown in FIG. 9, the first barrel 215 includes a passage 223 having the open end of the first barrel 215. The passage 223 may be defined by a substantially cylindrical wall. The passage 223 slidingly receives the second barrel 219 through the open end of the first barrel 215, and the second barrel 219 is movable between an extended position and a compressed position.

Figure 10:
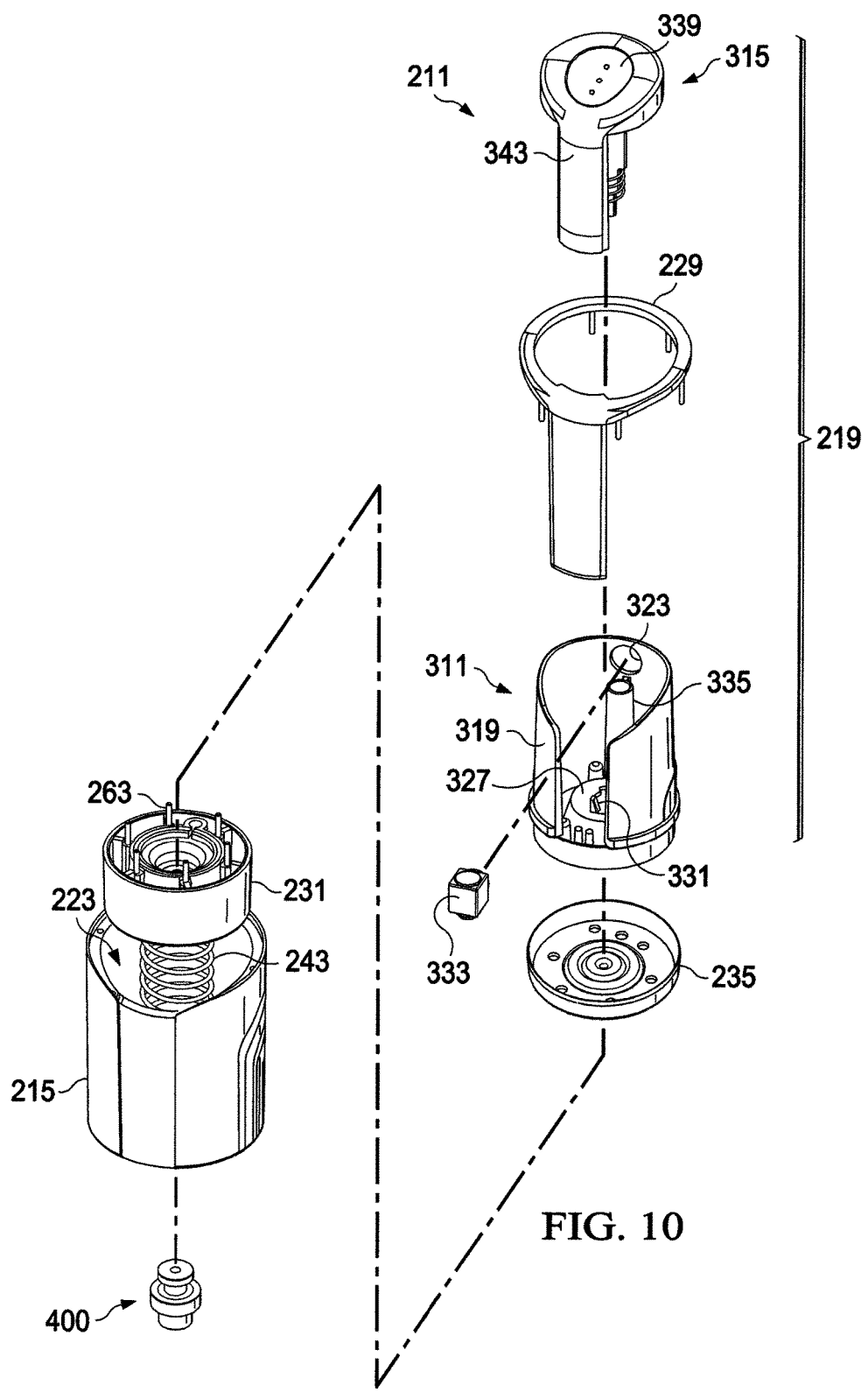
FIG. 10 is an exploded rear perspective view of the reduced pressure treatment apparatus of FIG. 7.

FIG. 10 is another exploded view, illustrating additional details that may be associated with the reduced-pressure source 211 in some embodiments. As shown in FIGS. 9 and 10, the reduced-pressure source 211 further includes a piston 231 and a seal 235. If the reduced-pressure source 211 is assembled, the piston 231 and the seal 235 are slidingly received within the passage 223 of the first barrel 215. Both the piston 231 and the seal 235 are positioned in the passage 223 between the second barrel 219 and an end of the first barrel 215 opposite the open end of the first barrel 215, the seal 235 being positioned between the second barrel 219 and the piston 231.

Figure 11:
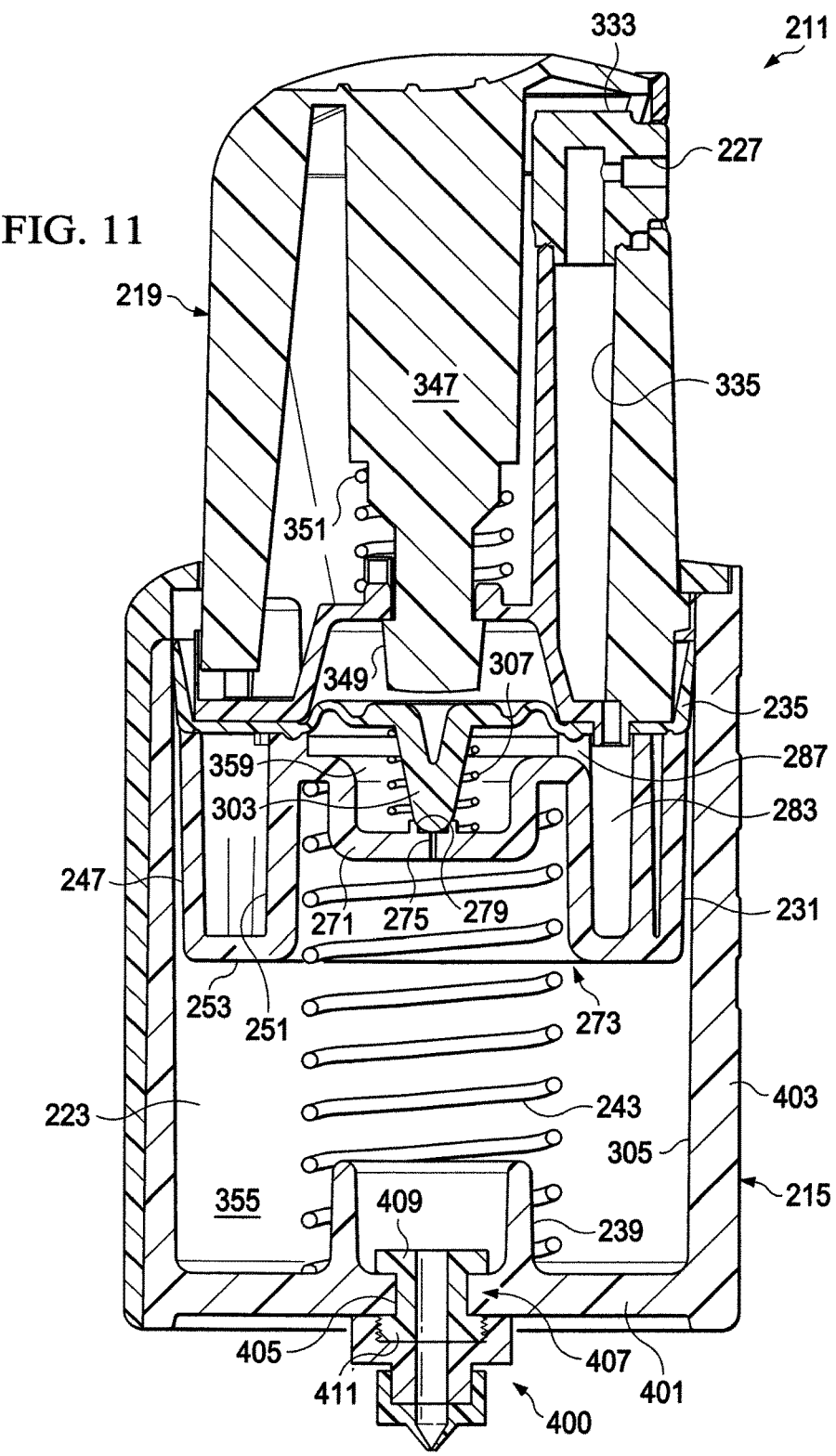
FIG. 11 is a cross-sectional view of the reduced pressure treatment apparatus in a first position taken at line 11-11 of FIG. 8.

FIG. 11 is a sectional view, illustrating additional details of the reduced-pressure source 211. The first barrel 215 includes a closed end opposite the open end of the first barrel 215. The closed end of the first barrel 215 may be formed by an outer wall 401 having a peripheral portion joined to a cylindrical wall 403 forming the passage 223. The outer wall 401 may also have a valve assembly 400 disposed within the outer wall 401. The first barrel 215 includes a protrusion 239 extending from the outer wall 401 of the first barrel 215 into the passage 223. A piston spring 243 or other biasing member may be positioned within the passage 223, and the protrusion 239 receives an end of the piston spring 243. The protrusion 239 can reduce lateral movement of the piston spring 243 within the passage 223. The piston 231 may receive an opposite end of the piston spring 243. The piston spring 243 biases the piston 231, the seal 235, and the second barrel 219 toward the extended position illustrated in FIG. 11.

Figure 12:
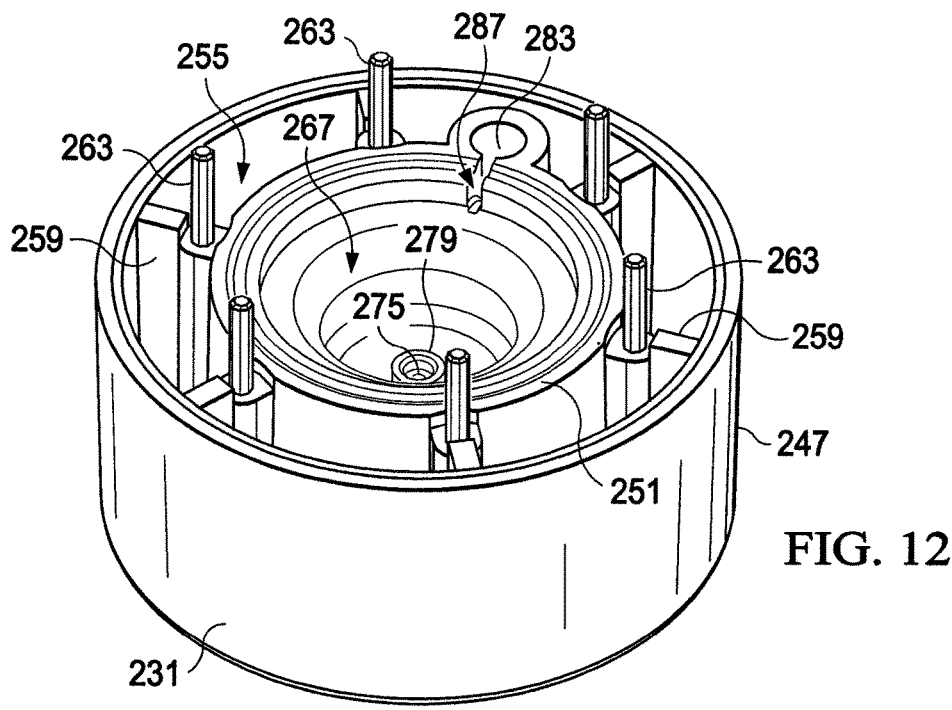
FIG. 12 is a top-rear perspective view of a piston of the reduced pressure treatment apparatus of FIG. 7.
Figure 13:
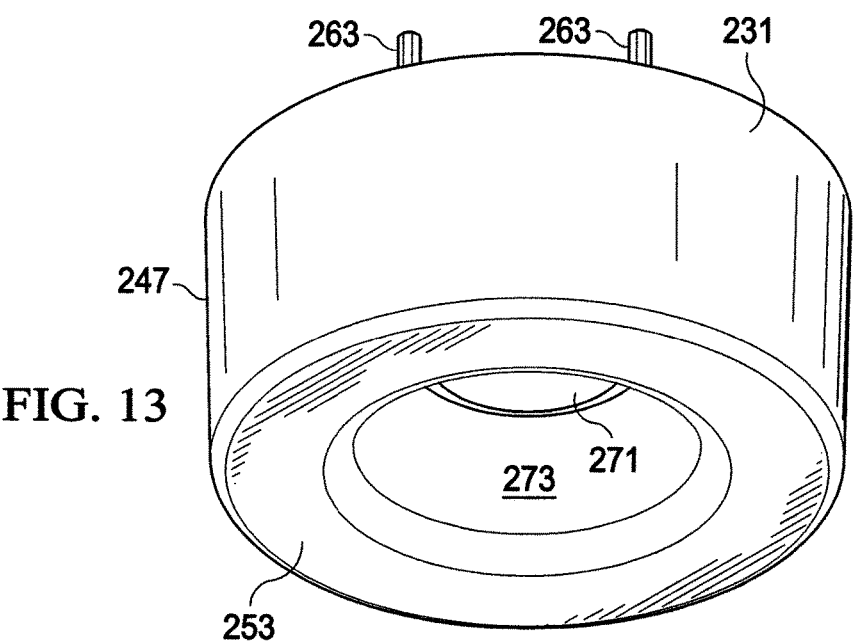
FIG. 13 is a bottom-rear perspective view of the piston of FIG. 12.

FIG. 12 and FIG. 13 are perspective views illustrating additional details of the piston 231. The piston 231 includes an outer wall 247 and an inner wall 251 joined by an outer floor 253. An annulus 255 is defined between the outer wall 247 and the inner wall 251, and a plurality of radial supports 259 are positioned between the outer wall 247 and the inner wall 251 in the annulus 255. The radial supports 259 provide additional rigidity to the piston 231. The presence of the annulus 255 as well as the sizes and spacing of the radial supports 259 within the annulus 255 reduces the weight of the piston 231 as compared to a single-wall piston that includes no annulus. However, it should be apparent that either piston design would be suitable for the reduced-pressure source described herein.

A plurality of guides 263 are disposed on the piston 231, and in some embodiments, a guide 263 can be disposed on each radial support 259. As described in more detail herein, the guides 263 serve to align the piston 231 relative to the seal 235 and the second barrel 219. The guides 263 further serve to secure the piston 231 to the second barrel 219 by means of a friction fit.

The piston 231 further includes an inner bowl 267 that is defined by the inner wall 251 and an inner floor 271. In some embodiments, the inner floor 271 may be two-tiered or multi-tiered as illustrated in FIG. 11, but the inner floor 271 may instead be single-tiered and/or substantially planar. The inner floor 271 may be positioned such that a recess 273 is defined beneath the inner floor 271 to receive an end of the piston spring 243 (see FIGS. 11 and 13). A regulator passage 275 passes through the inner floor 271 and may be seen in more detail in FIG. 11. A valve seat 279 may be positioned in the inner bowl 267 near the regulator passage 275 such that fluid communication through the regulator passage 275 may be selectively controlled by selective engagement of the valve seat 279 with a valve body (described in more detail with reference to FIG. 15).

A well 283 is positioned in the annulus 255 of the piston 231, and a channel 287 is fluidly connected between the well 283 and the inner bowl 267. The channel 287 allows fluid communication between the well 283 and the inner bowl 267.

Figure 14:
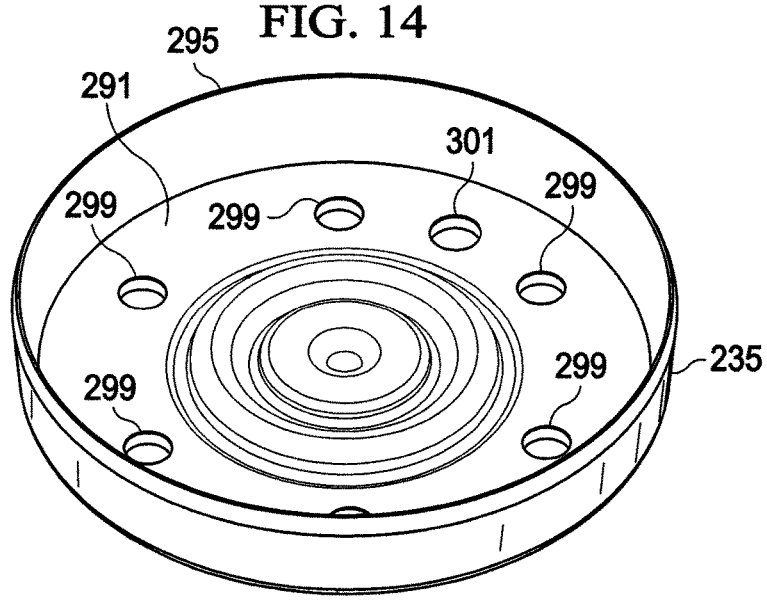
FIG. 14 is a top-rear perspective view of a seal of the reduced pressure treatment apparatus of FIG. 7.
Figure 15:
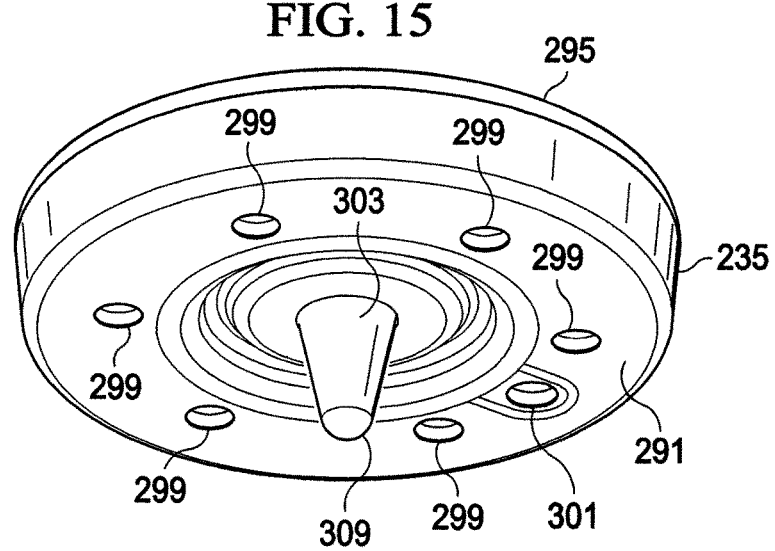
FIG. 15 is a bottom-rear perspective view of the seal of FIG. 14.

FIG. 14 and FIG. 15 are perspective views illustrating additional details of the seal 235. The seal 235 includes a central portion 291 that is circumscribed by a skirt portion 295. A plurality of guidance apertures 299 are disposed in the central portion 291 to receive the guides 263 of the piston 231 when the reduced-pressure source 211 is assembled. A communication aperture 301 is similarly disposed in the central portion 291, and in some embodiments, the communication aperture 301 is radially spaced an equal distance from a center of the seal as the guidance apertures 299. The communication aperture 301 permits fluid communication through the central portion 291 of the seal 235 and with the well 283 of the piston 231 upon assembly.

The skirt portion 295 of the seal 235 extends axially and radially outward from the central portion 291. As illustrated in FIG. 11, the skirt portion 295 engages an inner surface 305 of the first barrel 215 to permit unidirectional fluid communication past the seal 235. The skirt portion 295 of the seal 235 may allow fluid to flow past the skirt portion 295 if the fluid flow is directed from the side of the seal 235 on which the piston 231 is disposed toward the opposite side of the seal 235. The skirt portion 295 may substantially prevent fluid flow in the opposite direction. While the skirt portion 295 of the seal 235 effectively controls fluid communication past the skirt portion 295, a valve member such as, for example, a check valve or other valve may be used to control fluid flow.

As illustrated in more detail in FIGS. 11 and 15, a valve body 303 is positioned on the central portion 291 of the seal 235. The valve body 303 may depend from the central portion 291 in an axial direction opposite the skirt portion 295. Although valve bodies of many types, shapes and sizes may be used, the valve body 303 may be cone-shaped with an apex 309 that is adapted to sealingly engage the valve seat 279 of the piston 231. While the valve body 303 is illustrated as being an integral part of the seal 235, the valve body 303 may be a separate component from the seal 235 that is provided to engage the valve seat 279.

In some embodiments, both the seal 235 and the valve body 303 are made from an elastomeric material, which could include without limitation a medical grade silicone. While many different materials may be used to construct, form, or otherwise create the seal 235 and the valve body 303, a flexible material may be used to improve the sealing properties of the skirt portion 295 with the inner surface 305 and the valve body 303 with the valve seat 279.

Figure 20:
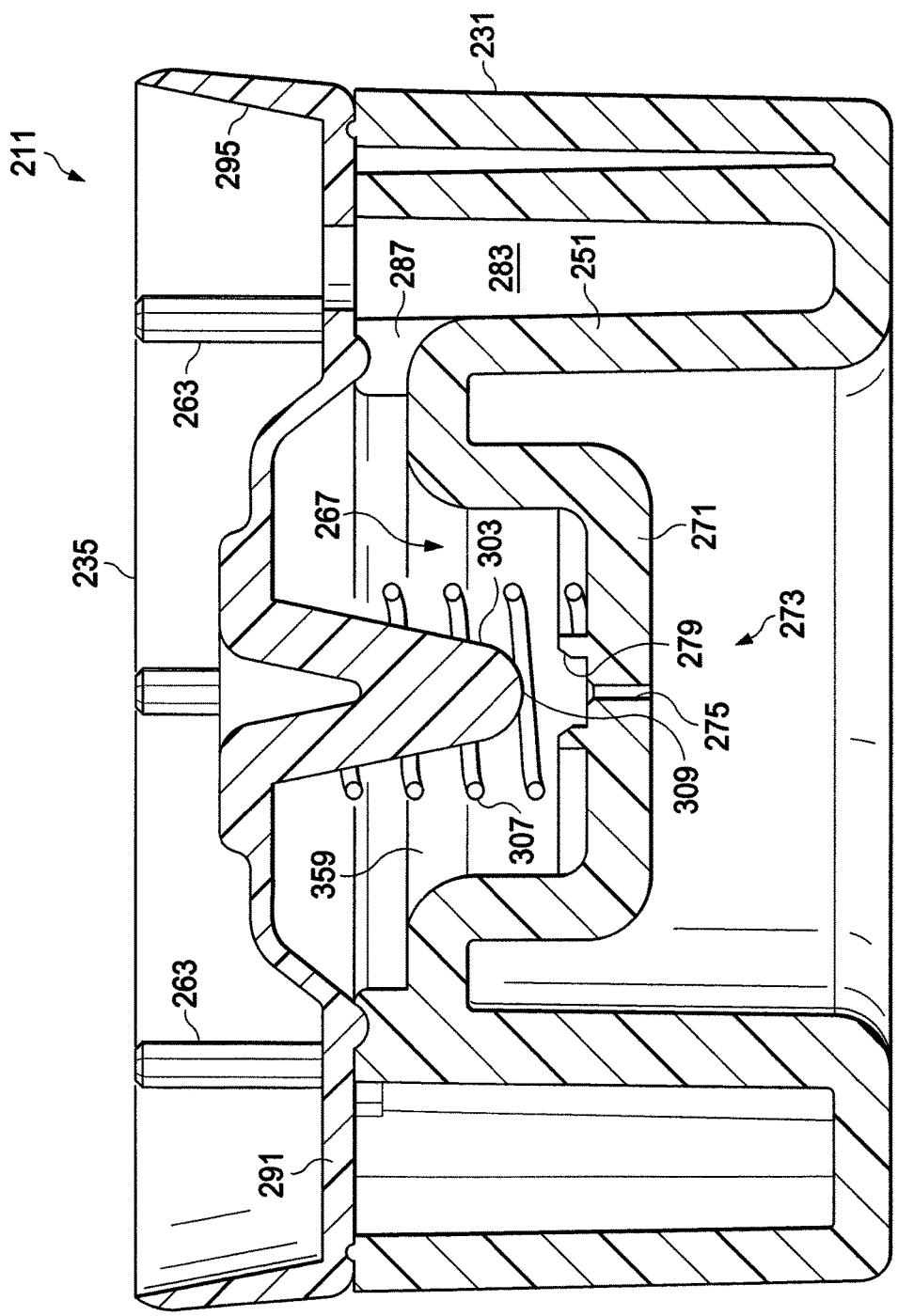
FIG. 20 is an enlarged cross-sectional view of the reduced pressure treatment apparatus of FIG. 19 with the valve body shown in an open position.
Figure 20A:
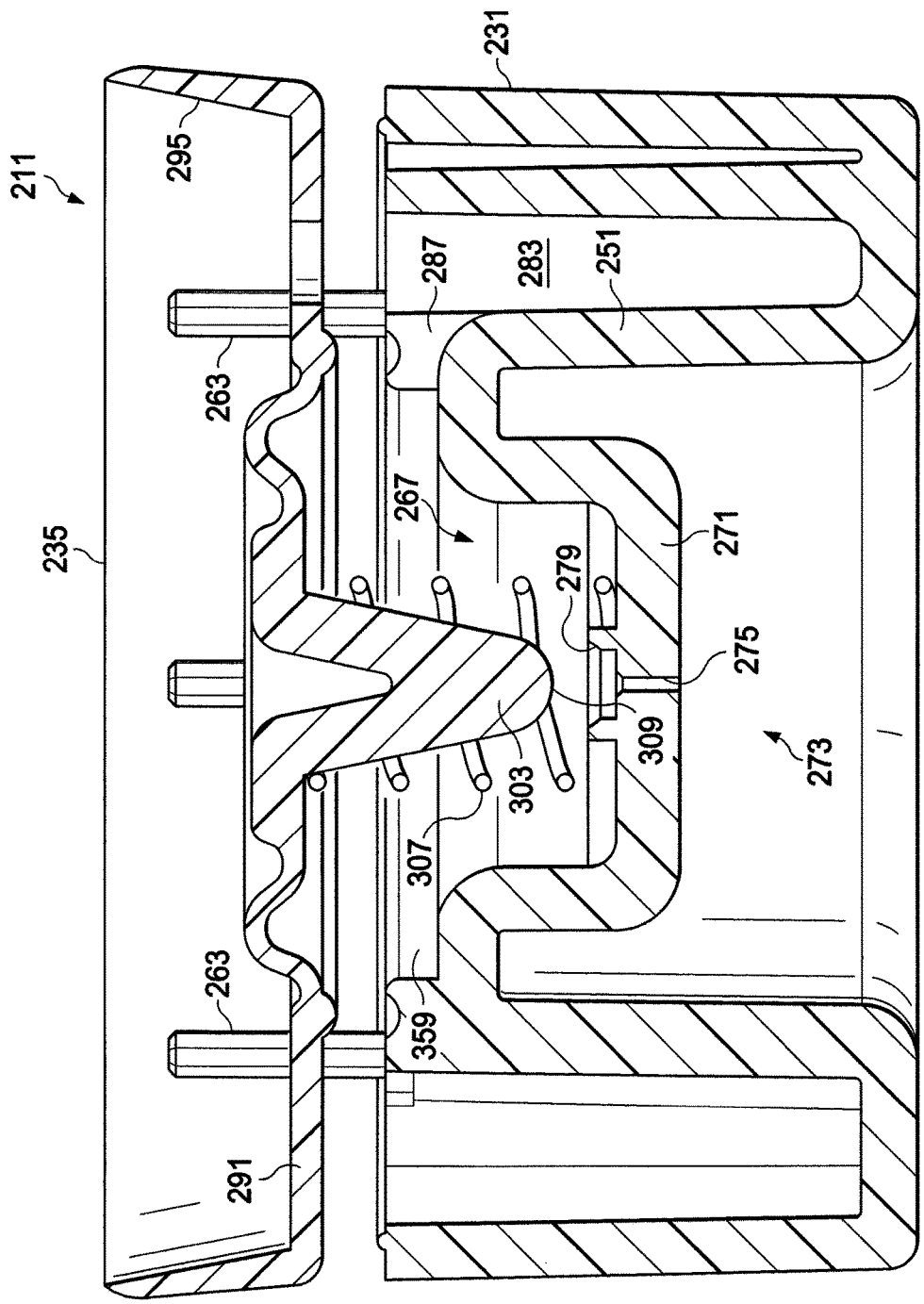
FIG. 20A is an enlarged cross-sectional view, similar to that of FIG. 20, of a reduced pressure treatment apparatus according to an exemplary embodiment.

Referring more specifically to FIG. 11, a regulator spring 307 is provided to bias the valve body 303 away from the piston 231 and the valve seat 279. One end of the regulator spring 307 may be positioned concentrically around the valve seat 279 within the inner bowl 267 of the piston 231, while another end of the regulator spring 307 may be positioned around the valve body 303. The biasing force provided by the regulator spring 307 urges the valve body 303 toward an open position in which fluid communication is permitted through the regulator passage 275. FIG. 20 is a sectional view, illustrating additional details of the piston 231 and the seal 235. In the exemplary embodiment, if the spring 307 biases the valve body 303 toward the open position, only the central portion 291 of the seal 235 moves upward due to the flexibility of the seal. FIG. 20A is a sectional view, illustrating additional details of another embodiment of the piston 231 and the seal 235. In the exemplary embodiment, the biasing force of the spring 307 may move the entire seal 235 toward the open position.

Figure 16:
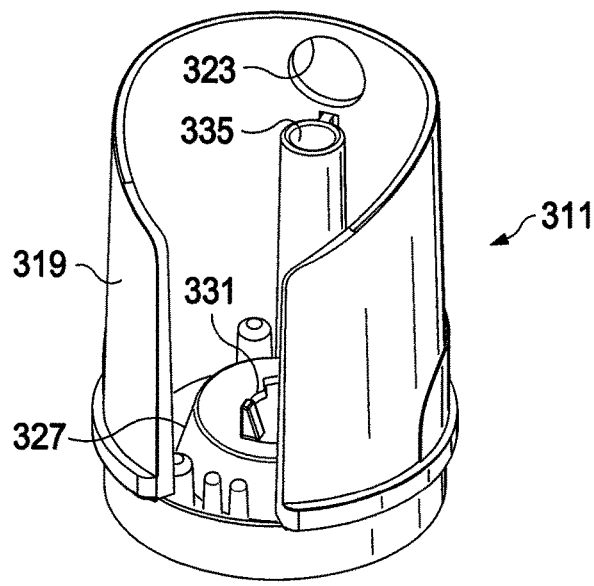
FIG. 16 is a top-rear perspective view of a portion of a second barrel of the reduced pressure treatment apparatus of FIG. 7.

As shown in FIGS. 9-11, the second barrel 219 includes a first housing portion 311 and a second housing portion 315. FIG. 16 is a perspective view, illustrating additional details of the first housing portion 311 of the second barrel 219. The first housing portion 311 includes an outer shell 319 having an aperture 323 disposed near an open end of the first housing portion 311. A floor 327 is integrally formed with or otherwise connected to the outer shell 319 on an end of the first housing portion 311 opposite the open end. A passage 331 may be centrally disposed in the floor 327. Referring to FIG. 9 and FIG. 11, a boss 333 is integrated with or connected to the first housing portion 311. The boss 333 includes the outlet port 227, which is physically aligned with the aperture 323 to allow a delivery tube to be fluidly connected to the outlet port 227. In some embodiments, the boss 333 is a ninety degree fluid fitting that permits the outlet port 227 to fluidly communicate with a conduit 335 positioned within the first housing portion 311. The conduit 335 may be a rigid conduit that is formed from the same or similar material to that of the outer shell, or in another embodiment, the conduit 335 may be flexible.

Figure 17:
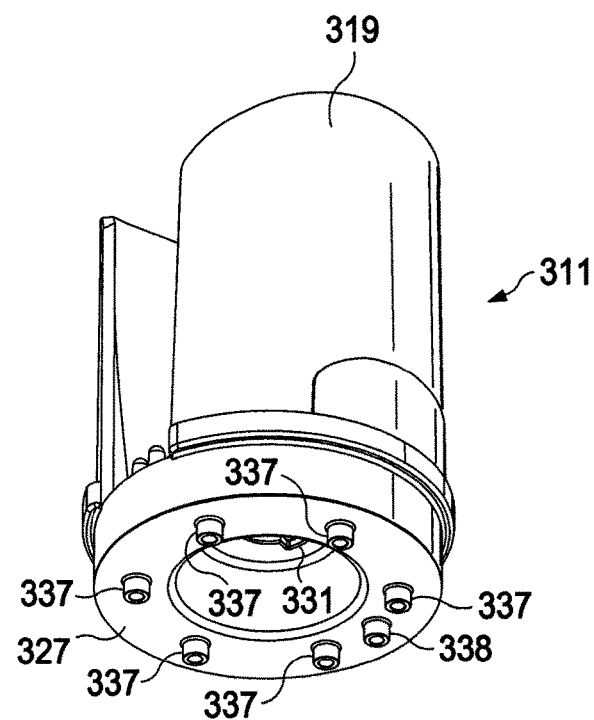
FIG. 17 is a bottom-rear perspective view of the portion of the second barrel of FIG. 16.

FIG. 17 is another perspective view, illustrating additional details of the first housing portion 311. The first housing portion 311 includes a plurality of guidance apertures 337 that are disposed in the floor 327 of the first housing portion 311. When the reduced-pressure source 211 is assembled, the guidance apertures 337 receive the guides 263 of the piston 231 to ensure that the second barrel 219 remains aligned with the piston 231. A friction fit between the guides 263 and the guidance apertures 337 assists in securing the relative positions of the piston 231 and the second barrel 219. It should be readily apparent, however, that the piston 231 and the second barrel 219 may be secured by other means. A communication aperture 338 is also disposed in the floor 327 to allow fluid communication with the conduit 335 through the floor 327.

Referring to FIGS. 9 and 10, the second housing portion 315 may include an end cap 339 integrally or otherwise connected to a guide 343. Together, the end cap 339 and the guide 343 slidingly engage the outer shell 319 of the first housing portion 311 to create a substantially closed second barrel 219 (with the exception of various apertures and passages described herein). While the second barrel 219 may be constructed from fewer components, the first housing portion 311 and the second housing portion 315 allows easier access within the second barrel 219 and also allows easier assembly of the reduced-pressure source 211. Additional advantages regarding the sliding engagement of the first housing portion 311 and the second housing portion 315 are explained in more detail below.

A shaft 347 extends from the end cap 339 and includes an engagement end 349 opposite the end cap 339. When the second barrel 219 is assembled, the shaft 347 may be substantially coaxial to a longitudinal axis of the second barrel 219 and extend through the passage 331 in the floor 327 of the first housing portion 311. A spring 351 is positioned within the second barrel 219 such that one end of the spring 351 bears upon the floor 327 of the first housing portion 311 and another end of the spring 351 bears upon the shaft 347 or another portion of the second housing portion 315. The spring 351 biases the shaft 347 and other portions of the second housing portion 315 toward a disengaged position (see position of the shaft 347 in FIG. 11) in which the engagement end 349 of the shaft 347 does not bear upon the seal 235 or the valve body 303. The sliding relationship and engagement between the first housing portion 311 and the second housing portion 315 allows a user to exert a force on the second housing portion 315 (against the biasing force of the spring 351) to move the second housing portion 315 to an engaged position. In the engaged position, the engagement end 349 of the shaft 347 bears upon the seal 235 above the valve body 303 (see FIG. 18), which forces the valve body 303 against the valve seat 279, thereby preventing fluid communication through the regulator passage 275.

When the reduced-pressure source 211 is assembled, as illustrated in FIG. 11, a charging chamber 355 is defined within the first barrel 215 beneath the piston 231. A regulated chamber 359 is defined within the inner bowl 267 of the piston 231 beneath the seal 235. The regulator passage 275 allows selective fluid communication between the charging chamber 355 and the regulated chamber 359 depending on the position of the valve body 303. The regulated chamber 359 fluidly communicates with the well 283 of the piston 231 through the channel 287. The well 283 is aligned with the communication aperture 301 of the seal 235 and the communication aperture 338 of the first housing portion 311, which allows fluid communication between the well 283 and the conduit 335 and the outlet port 227 of the second barrel 219.

While the regulator passage 275 is illustrated as being disposed within the piston 231, the regulator passage 275 could instead be routed through the wall of the first barrel 215. The regulator passage 275 could be any conduit that is suitable for allowing fluid communication between the regulated chamber 359 and the charging chamber 355.

In operation, the reduced-pressure source 211 is capable of being used with other components of a reduced pressure treatment system similar to those of reduced pressure treatment system 100 (see FIG. 1). The outlet port 227 of the reduced-pressure source 211 is adapted to be connected to a delivery tube or other conduit that is fluidly connected to a tissue site. Although a fluid canister could be integrated into the reduced-pressure source 211, in some embodiments, the reduced-pressure source 211 is not intended to collect wound exudates or other fluids within any internal chamber. In some embodiments, the reduced-pressure source 211 may either be used with low-exudating wounds, or an alternative collection system such as an external canister or absorptive dressing may be used to collect fluids.

Figure 18:
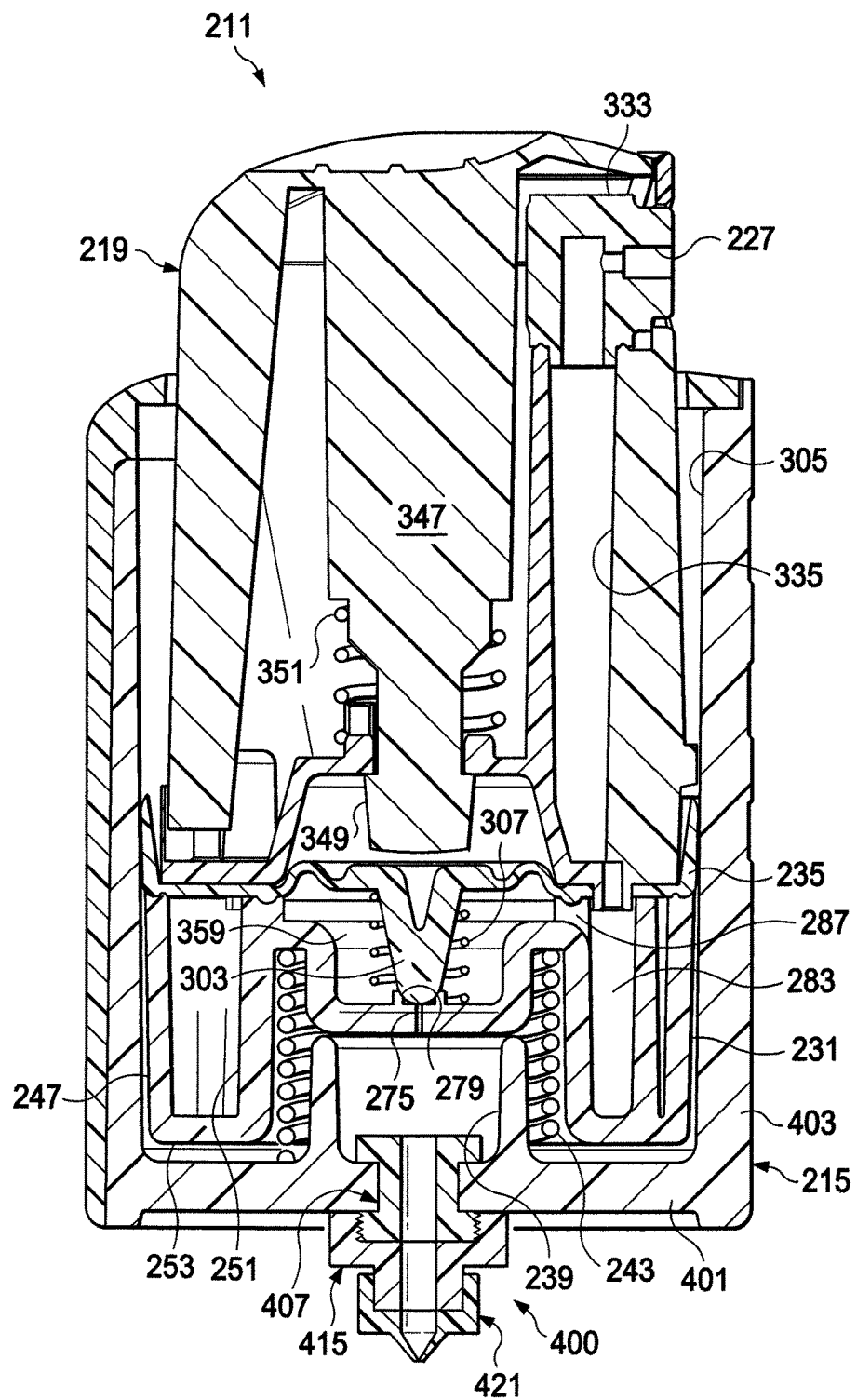
FIG. 18 is a cross-sectional view of the reduced pressure treatment apparatus in a second position taken along line 11-11 of FIG. 8.

Referring to FIG. 11 additional details of the reduced-pressure source 211 in the extended position are shown. To charge the reduced-pressure source 211, the second barrel 219 can be manually compressed into the first barrel 215 by a user such that the reduced-pressure source 211 is placed in a compressed position. Charging the reduced-pressure source 211 may also be referred to as priming the reduced-pressure source 211. FIG. 18 is a sectional view, illustrating additional details of the reduced-pressure source 211 in the compressed position. The force exerted by the user on the second barrel 219 to place the reduced-pressure source 211 in the compressed position of FIG. 18 must be greater than the biasing force provided by the piston spring 243. As the second barrel 219 compresses within the first barrel 215 and moves toward the closed end of the first barrel 215, the force being exerted on the second barrel 219 by the user is also transmitted to the seal 235 and the piston 231. The movement of the second barrel 219, the seal 235, and the piston 231 into the compressed position decreases the volume of the charging chamber 355. As the volume of the charging chamber 355 decreases, the pressure in the charging chamber 355 increases, but air and other gases within the charging chamber 355 are allowed to escape past the skirt portion 295 of the seal 235 due to the increased pressure within the charging chamber 355.

If the user releases the compressive force exerted upon the second barrel 219, the biasing force exerted by the piston spring 243 on the piston 231 moves the piston 231, the seal 235, and the second barrel 219 toward the extended position. As this movement occurs, the volume of the charging chamber 355 increases. Since the skirt portion 295 of the seal 235 allows only unidirectional flow, air and other gases are not permitted to enter the charging chamber 355 past the skirt portion 295. A resulting drop in pressure (i.e., a generation of reduced pressure) occurs within the charging chamber 355 as the volume increases. The amount of reduced pressure generated within the charging chamber 355 is dependent on the spring constant of the piston spring 243 and the integrity of the seal 235. In some embodiments, it is desired to generate a reduced pressure that is greater (i.e., a lower absolute pressure) than the therapy pressure to be supplied to the tissue site. For example, if it is desired to provide 125 mm Hg of reduced pressure to the tissue site, it may be desirable to have the charging chamber 355 charged to 150 mm Hg of reduced pressure.

Figure 19:
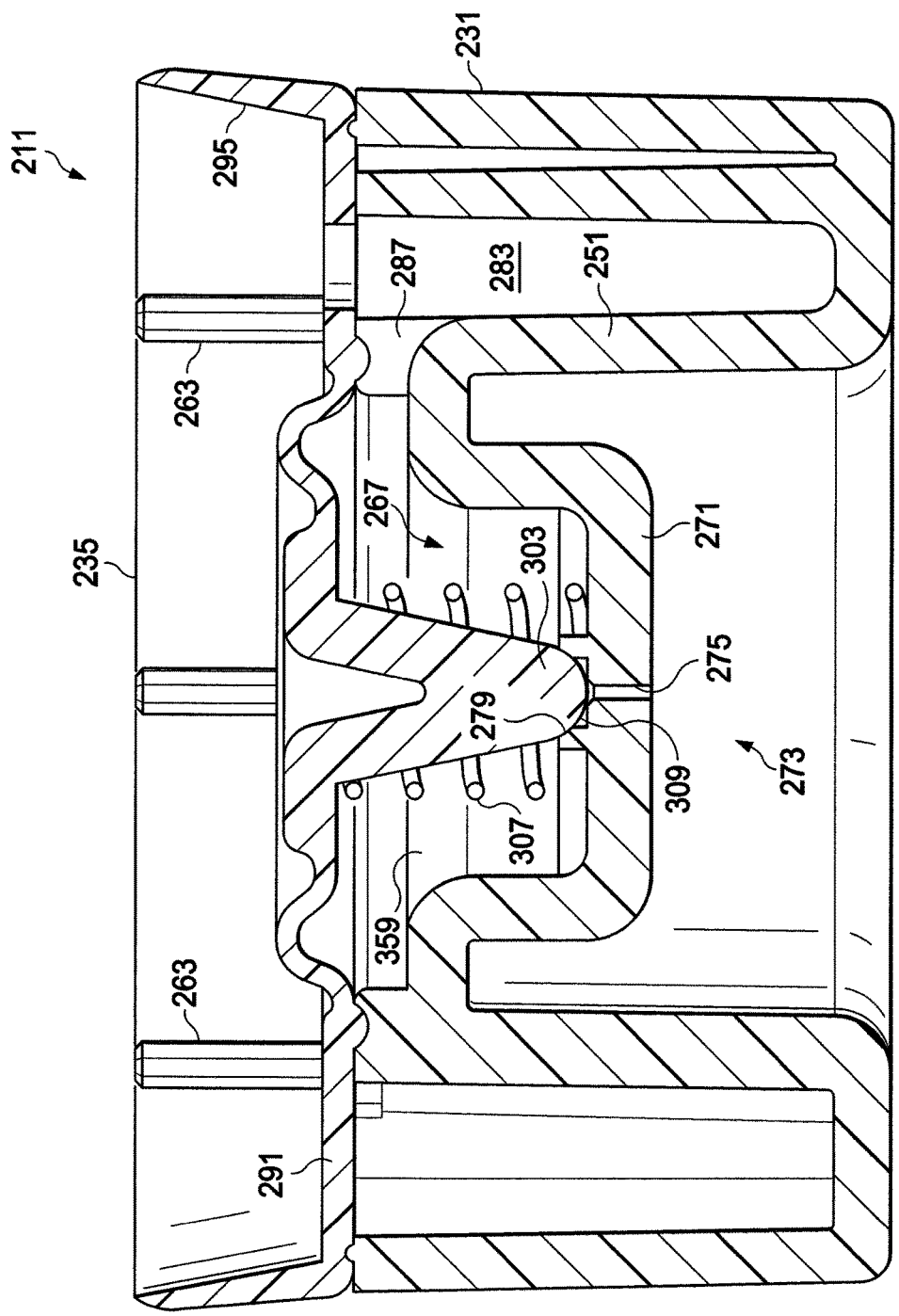
FIG. 19 is an enlarged cross-sectional view of the reduced pressure treatment apparatus of FIG. 18, the reduced pressure treatment apparatus having a valve body shown in a closed position.

The regulated chamber 359 provides the desired therapy pressure that is delivered to the outlet port 227 and the tissue site. If the reduced pressure within the charging chamber 355 is greater than the reduced pressure within the regulated chamber 359 and if the reduced pressure in the regulated chamber 359 is less than the desired therapy pressure, the upward force on the seal 235 (exerted by the increased absolute pressure in the regulated chamber 359 and the biasing force of the regulator spring 307, both against the atmospheric pressure exerted downward on the seal 235) moves the valve body 303 into the open position (see FIG. 20), thereby allowing fluid communication between the charging chamber 355 and the regulated chamber 359. The charging chamber 355 continues to charge the regulated chamber 359 with reduced pressure (i.e., the absolute pressure in the regulated chamber 359 continues to drop) until the reduced pressure in the regulated chamber 359, balanced against the atmospheric pressure above the seal 235, is sufficient to counteract the biasing force of the regulator spring 307 and move the valve body into the closed position. FIG. 19 is a sectional view, illustrating additional details of the seal 235 and the piston 231 in the closed position. If the regulated chamber 359 is charged with the desired therapy pressure, this pressure may be delivered to the outlet port 227 as detailed previously.

When the reduced-pressure source 211 is initially connected to a delivery tube and tissue site for treatment, it may be necessary to compress the second barrel 219 within the first barrel 215 multiple times. As each compression stroke is completed, the reduced pressure generated within the charging chamber 355 will pull air and any other gases from the delivery tube and the tissue site until the pressure within the tube and at the tissue site begins to approach the desired therapy pressure.

As the reduced-pressure source 211 is being primed by one or more compressions, it is important that air and other positively-pressurized gases being pushed out of the charging chamber 355 are pushed past the skirt portion 295 of the seal 235 and not into the regulated chamber 359. Positively pressurized gas flow to the regulated chamber 359 may transfer to the delivery tube and the tissue site, which would counteract the reduced pressure that is then being applied to the tissue site. To prevent positively pressurized gas from entering the regulated chamber 359, the shaft 347 is provided to engage the seal 235 and valve body 303. As the second barrel 219 is compressed within the first barrel 215, the second housing portion 315 moves relative to the first housing portion 311 so that the shaft 347 exerts a force on the valve body 303 that holds the valve body 303 in the closed position. Since the shaft 347 remains engaged during the entire compression, or charging stroke, of the reduced-pressure source 211, the air within the charging chamber 355 is vented past the seal 235 and not into the regulated chamber 359.

While the reduced-pressure source 211, including the first barrel 215, the second barrel 219, the piston 231, and the seal 235, have been described herein as being cylindrical, it will be readily apparent that all of these components may be other sizes or shapes. Additionally, the relative positions of the valve seat 279 and the valve body 303 may be reversed such that the valve body 303 is positioned below the valve seat 279.

If a dressing, delivery tube, or other component has a small leak, the valve body 303 can maintain a therapeutic pressure. For example, the regulated chamber 359 may be adapted to compensate for leaks that are less than about 1 L/min. However, the valve body 303 may not be able to maintain the therapy pressure if a leak exceeds such a limit, which is generally dependent upon the size of the restrictions on the entry and exit sides of the regulated chamber 359. In some embodiments, for example, where the charging chamber 335 is charged by an external reduced-pressure source, the regulated chamber 359 may compensate for a leak of about 1 L/min. In other embodiments, for example, where the charging chamber 335 is charged manually without the assistance of an external reduced-pressure source, the regulated chamber 359 may compensate for a leak of about several mL/hour.

The flow leaving regulated chamber 359 can be controlled by adjusting the bore size of regulator passage 275, and the flow coming into the regulated chamber 359 can be controlled by adjusting the size of the bore of a number of components in the fluid path, such as the conduit 112, tubing adapter 116, or outlet port 227. The size of the bores can be balanced such that a flow-induced drop in reduced pressure partially opens the valve body 303 if there is a leak in the dressing that exceeds a predetermined or configurable leak threshold, leaving a gap between the valve body 303 and the regulator passage 275. In some exemplary embodiments, the gap between the valve body 303 and the regulator passage 275 is less than about 0.1 mm. Optionally, the bore sizes can be balanced so that the valve body 303 remains open if no dressing is connected. Moreover, the bore sizes may be calibrated such that a flow of air through the gap produces an audible indicator, alerting an operator of an unexpected loss of therapeutic pressure. For example, a leak threshold flow rate may represent a leak flow rate that is sufficient to interfere with a prescribed therapy, and many applications may have a leak threshold of about 0.8 L/min. An audible indicator may be produced at the leak threshold if the regulator passage 275 is in the range of about 1 mm to about 1.5 mm and the conduit 112 has a lumen size of about 1.2 mm over a length of about 500 mm to 800 mm. The size of the gap (e.g., the distance between the apex 309 and the regulator passage 275) may be calibrated so that the pitch of the audible note changes as flow decreases or increases, thereby differentiating the size or rate of a leak.

Generally, if the lumen size of the conduit 112 is held constant at about 1.7 mm over a length of about 500 mm to 800 mm, a reduction in the size of the diameter of the regulator passage 275 may raise the leak threshold flow rate to initiate the audible warning. Similarly, if the size of the diameter of the regulator passage 275 is increased, the leak threshold flow rate to initiate the audible warning may be lowered. In some embodiments, the lumen size of the conduit 112 is about 1.7 mm and the diameter of the passage 275 is about 0.7 mm; in response, the alarm threshold, the flow rate at which the audible warning may initiate, may be at approximately 1 L/min of flow. Although there may be large tolerances in the alarm threshold with the mechanical system described herein, flow between about 700 mL/min to about 1 L/min may cross the alarm threshold and result in an audible alert. Conventional electrical pump systems currently have an alarm triggered at a flow rate of approximately 1 L/min.

In other exemplary embodiments, the flow may be controlled with additional components, such as filters, which may include membranes, sintered porous materials, fibers, woven, or non-woven materials, for example. The valve body 303 and the regulator passage 275 may also be further designed to accentuate the audible feedback.

Figure 21:
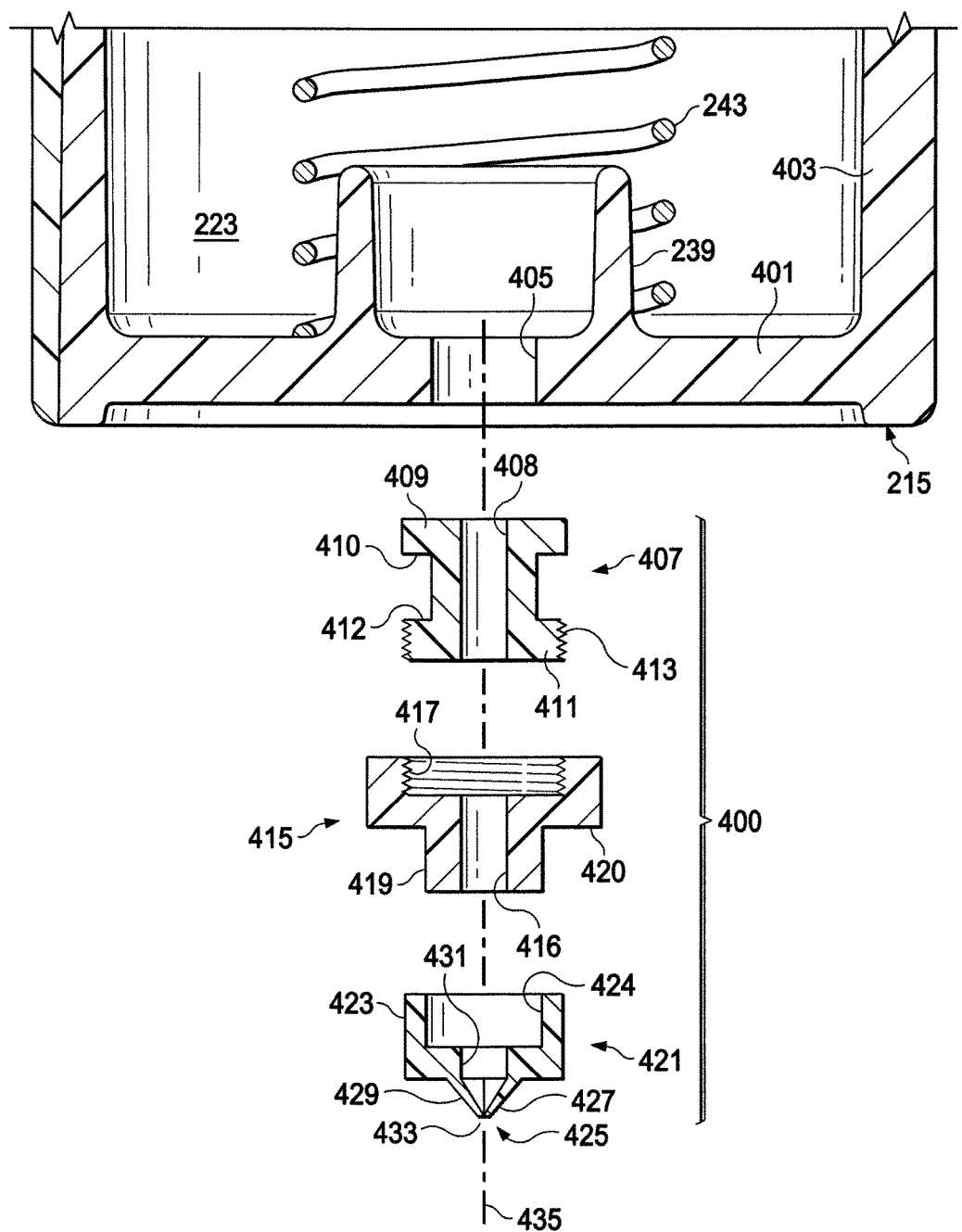
FIG. 21 is an exploded sectional view of a closed end of the reduced pressure treatment apparatus of FIG. 11.

In some embodiments, the valve assembly 400 may be used to charge the reduced-pressure source 211 without manual actuation. FIG. 21 is a sectional exploded view of the closed end of the charging chamber 355 of the first barrel 215 illustrating additional details of an embodiment of the valve assembly 400. In some embodiments, the outer wall 401 includes an aperture 405 proximate a center of the outer wall 401. The aperture 405 may extend through the outer wall 401 from the charging chamber 355 to the ambient environment around the first barrel 215. In some embodiments, the aperture 405 is coaxial with the piston spring 243 and the protrusion 239. In other embodiments, the aperture 405 is not coaxial with the piston spring 243 and the protrusion 239.

The valve assembly 400 may include a valve adapter 407, a high pressure adapter 415, and a valve 421. The valve adapter 407 may be a cylindrical body having an outer diameter substantially equal to a diameter of the aperture 405 and a length greater than or equal to a thickness of the outer wall 401. The valve adapter 407 may include a valve passage 408 extending the length of the valve adapter 407. The valve adapter 407 also may include a chamber flange 409 on a first end of the valve adapter 407. The chamber flange 409 may have an outer diameter that is greater than the outer diameter of the aperture 405 so that the chamber flange 409 may form an annular shoulder 410. The valve adapter 407 may further include a barrel flange 411 on a second end of the valve adapter 407 opposite the chamber flange 409. The barrel flange 411 may have an outer diameter greater than the outer diameter of the aperture 405 so that the barrel flange 411 may form an annular shoulder 412 facing the annular shoulder 410 of the chamber flange 409. In some embodiments, the chamber flange 409 and the barrel flange 411 have outer diameters that are approximately the same. In some embodiments, the barrel flange 411 may include a thread 413 on peripheral portion of the barrel flange 411.

The high pressure adapter 415 may be a generally cylindrical body having an adapter passage 416 extending through the high pressure adapter 415 from a first end to a second end. In some embodiments, the first end of the high pressure adapter 415 may have an outer diameter greater than the outer diameter of the barrel flange 411 and may include a cavity 417. The cavity 417 extends at least a portion of a distance from the first end of the high pressure adapter 415 toward the second end of the high pressure adapter 415 and may be coaxial with the adapter passage 416. The cavity 417 may have a depth greater than or equal to a thickness of the barrel flange 411, permitting the barrel flange 411 to be disposed within the cavity 417. In some embodiments, the wall of the cavity 417 may be threaded. In some embodiments, the thread of the wall of the cavity 417 may have a lead and a pitch configured to mate with the thread 413.

The high pressure adapter 415 also includes a neck portion, such as a nipple 419 disposed on the second end of the high pressure adapter 415 opposite the cavity 417. The nipple 419 may have a smaller outer diameter than the outer diameter of the first end of the high pressure adapter 415 proximate the cavity 417. An annular shoulder 420 may be formed at the union of the larger outer diameter of the cavity 417 with the smaller outer diameter of the nipple 419. In some embodiments, the annular shoulder 420 may face away from the cavity 417. In other embodiments, the high pressure adapter 415 may include a gradual transition from the cavity 417 to the nipple 419. The transition may be formed with a taper, for example.

In some embodiments, the valve 421 may be a duck-bill valve that includes a connector 423 on a first end and a duckbill, such as a flattened end 425, on a second end of the valve 421. The connector 423 may be tubular and form a valve cavity 424 extending from the first end of the valve 421 toward the flattened end 425. The cavity 424 may have an inner diameter substantially equal to the outer diameter of the nipple 419 of the high pressure adapter 415. The valve cavity 424 may terminate at an end of the connector 423. The end may be opposite an opening of the cavity 424 and may include a valve passage 431 extending through the end.

The flattened end 425 may be coupled to the closed end of the connector 423 proximate the valve passage 431. The flattened end 425 may have a first valve member 427 and a second valve member 429. The first valve member 427 may include a first end coupled to the closed end of the connector 423 and adjacent the valve passage 431. The second valve member 429 may include a first end coupled to the closed end of the connector 423 and adjacent to the valve passage 431. The first valve member 427 and the second valve member 429 may angle across the valve passage 431 so that second ends of the first valve member 427 and the second valve member 429 may contact over the valve passage 431. The first valve member 427 and the second valve member 429 may be coupled to the end of the connector 423 so that the first valve member 427 and the second valve member 429 circumscribe the valve passage 431. In some embodiments, the first valve member 427 and the second valve member 429 may each circumscribe a portion of the valve passage 431 and may have sides extending from the first end to the second end. In these embodiments, the sides of the first valve member 427 are coupled to the sides of the second valve member 429, preventing fluid communication between the first valve member 427 and the second valve member 429 along the sides of the first valve member 427 and the second valve member 429. In this manner, a slit 433 that is closeable may be formed between the second ends of the first valve member 427 and the second valve member 429. The valve 421 may be formed from a rubber or synthetic elastomer, for example.

Figure 22:
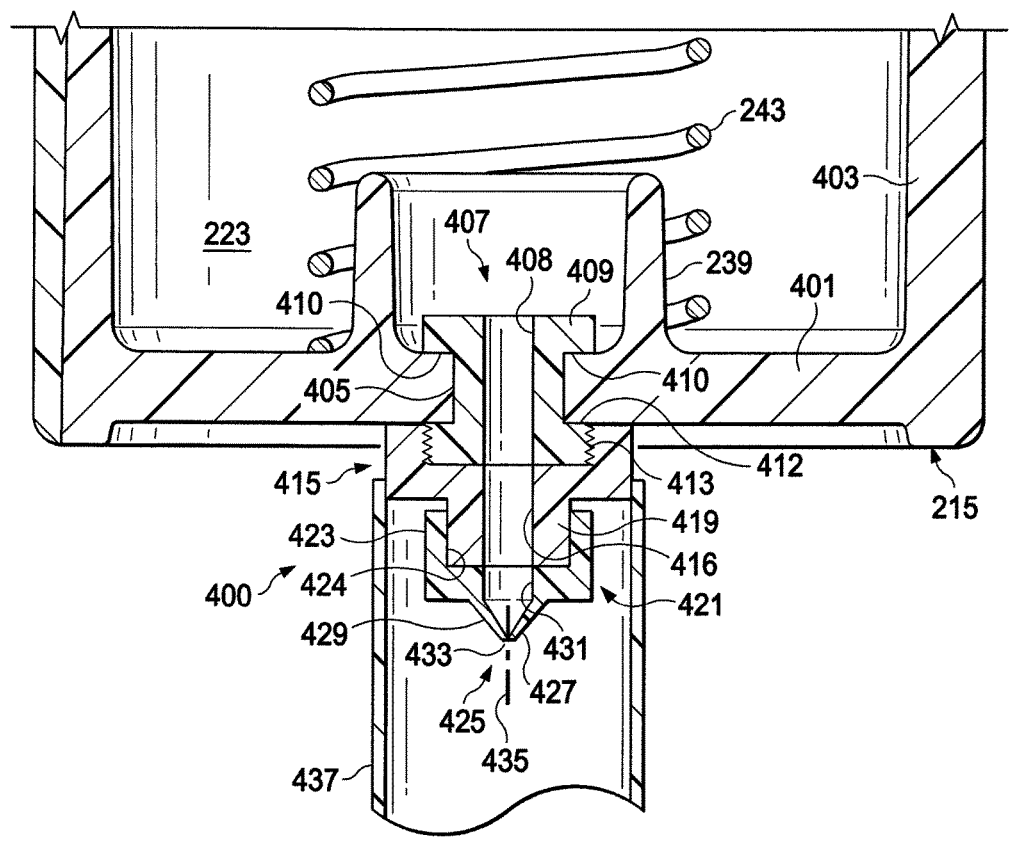
FIG. 22. is an assembled sectional view of the closed end of the reduced pressure treatment apparatus of FIG. 21.

FIG. 22 is a sectional view, illustrating additional details of the valve assembly 400. In some embodiments of FIG. 22, the valve assembly 400 is coupled to the reduced-pressure source 211. The valve assembly 400 may have the valve adapter 407 disposed within the aperture 405 so that the annular shoulder 410 of the chamber flange 409 abuts the surface of the outer wall 401 facing the charging chamber 355, and the annular shoulder 412 of the barrel flange 411 may abut the surface of the outer wall 401 facing away from the charging chamber 355. The annular shoulder 410 may engage the surface of the outer wall 401 facing the charging chamber 355, and the annular shoulder 412 may engage the surface of the outer wall 401 facing away from the charging chamber 355. In some embodiments, one or both of the chamber flange 409 and the barrel flange 411 may be secured, for example by welding, to the valve adapter 407 during assembly of the reduced-pressure source 211. For example, the valve adapter 407 may be formed with the chamber flange 409 on the first end and no flange on the second end. During assembly of the reduced-pressure source 211, the valve adapter 407 may be placed in the passage 223 and the second end of the valve adapter 407 may be inserted through the aperture 405 so that the annular shoulder 410 of the chamber flange 409 may engage the inner surface of the outer wall 401. The second end of the valve adapter 407 may protrude from the outer wall 401. The barrel flange 411 may then be coupled to the second end of the valve adapter 407. The barrel flange 411 may be coupled by welding, adhesives, with an interference fit, for example.

The cavity 417 of the high pressure adapter 415 may be threaded onto the thread 413 of the barrel flange 411 to secure the high pressure adapter 415 to the valve adapter 407. The cavity 424 of the connector 423 of the valve 421 may be fitted over the nipple 419 of the high pressure adapter 415 to secure the valve 421 to the high pressure adapter 415. In some embodiments, the cavity 424 of the connector 423 may be slightly smaller than the outer diameter of the nipple 419 so that the synthetic elastomer forming the valve 423 may, stretch around the nipple 419 and contract against the nipple 419 to secure the valve 421 to the nipple 419. In other embodiments, the first barrel 215 may be formed so that one or all of the valve adapter 407 and the high pressure adapter 415 may be integral to the first barrel 215. For example, the first barrel 215 may be formed to include at least the nipple 419 for attachment of the valve 421.

The slit 433 may allow fluid communication from the valve passage 431 to the ambient environment and may prevent fluid communication from the ambient environment to the valve passage 431. In some embodiments, the valve 421 may be formed of a material having sufficient strength to resist opening if introduced to pressures below a certain threshold. For example, the valve 421 may not permit fluid communication from the charging chamber 355 to a coupled external reduced-pressure source unless the supplied pressure is less than or equal to −150 mm Hg. In other embodiments, the first valve member 427 and the second valve member 429 may form an angle with an axis 435 of the valve passage 431. The angle may be selected such that a supplied pressure greater than a threshold pressure urges the second ends of the first valve member 427 and the second valve member 429 into tighter contact, preventing fluid flow through the slit 433. In an exemplary embodiment, the threshold pressure may be greater than or equal to the ambient pressure. In other embodiments, the threshold pressure may be less than the ambient pressure.

In operation, an external reduced-pressure source 437, such as an electrically driven pump or a wall-suction source, may be fluidly coupled to the reduced-pressure source 211. In some embodiments, the external reduced-pressure source 437 may be coupled to the high pressure adapter 415. In still other embodiments, the external reduced pressure source 437 is fluidly coupled to the valve 421. The external reduced-pressure source 437 may be activated to generate reduced pressure that may be supplied to the valve assembly 400. The valve 421 may open in response to a supplied pressure that is less than the pressure in the charging chamber 355, at least partially evacuating the charging chamber 355 through the valve passage 408, the adapter passage 416, and the valve passage 431. The evacuation of the charging chamber 355 may charge the reduced-pressure source 211, allowing operation of the reduced-pressure source 211 as described above.

In some embodiments, a wall-suction source may be coupled to the high pressure adapter 415 or the closed end of the first barrel 215. In these embodiments, the valve 421 may be disposed within a conduit or delivery tube. Reduced pressure may be supplied to the valve assembly 400, causing the valve 421 to open and permit fluid communication between the wall-suction source and the charging chamber 355 through the valve 421, the high pressure adapter 415, and the valve adapter 407. The fluid communication will at least partially evacuate the charging chamber 355, overcoming the force of the piston spring 243 and drawing the second barrel 219 into the first barrel 215, moving the second barrel 219 from the extended position illustrated in FIG. 11 to the compressed position illustrated in FIG. 18. The movement of the second barrel 219 into the first barrel 215 may provide an indication to a caregiver or the user that reduced pressure is being supplied to the reduced-pressure source 211. The seal 235 may operate as described above to regulate the supply of the reduced pressure from the charging chamber 355 to the dressing or tissue site. The valve body 303 will open and close the regulator passage 275 as described above to draw the dressing down and achieve therapeutic pressure at the tissue site.

The drawing of the second barrel 219 into the first barrel 215 and the compression of the piston spring 243 may create a stored reserve of reduced pressure. For example, once therapeutic pressure is achieved at the tissue site, the wall suction source may be uncoupled from the reduced-pressure source 211. The valve 421 may close, sealing the charging chamber 335 and maintaining the reduced-pressure source 211 in the compressed position of FIG. 18. The piston spring 243 may remain compressed providing stored energy that may continue to supply reduced pressure, as described above, if a leak is present in the system.

The reduced-pressure source 211 may also indicate the presence of a leak. For example, if there is a significant leak in the dressing at drawdown or during therapy, the second barrel 219 may not remain in the compressed position within the first barrel 215, indicating to the user or the caregiver that there may be a leak at the dressing. As the reduced pressure in the regulated chamber 359 approaches the ambient pressure at the tissue site due to the leak, the spring force of the spring 307 will overcome the combined force of the ambient pressure pushing down on the valve body 303 and the reduced pressure in the regulated chamber 359 pulling down on the valve body 303, allowing fluid flow through the regulator passage 275. In turn, the reduced pressure supplied to the charging chamber 355 may not be sufficient to overcome the force of the piston spring 243, allowing the second barrel 219 to move to the extended position of FIG. 11. This can provide the user with an indication that there is a leak.

In some embodiments, the reduced pressure supplied by the wall-suction source will be sufficient to maintain reduced pressure at the dressing or tissue site. In these embodiments, the regulated chamber 359 and the valve body 303 can operate to continue to supply reduced pressure to the tissue site. In some embodiments, the continued operation may have a flow through the regulator passage 275 that crosses the leak threshold, providing an audible alert to the user or the caregiver that there is a leak. If desired, the user or caregiver may depress the end cap 339 to hold the valve body 303 against the passage 275 to silence or mute the audible alert while the leak is addressed.

Figure 23:
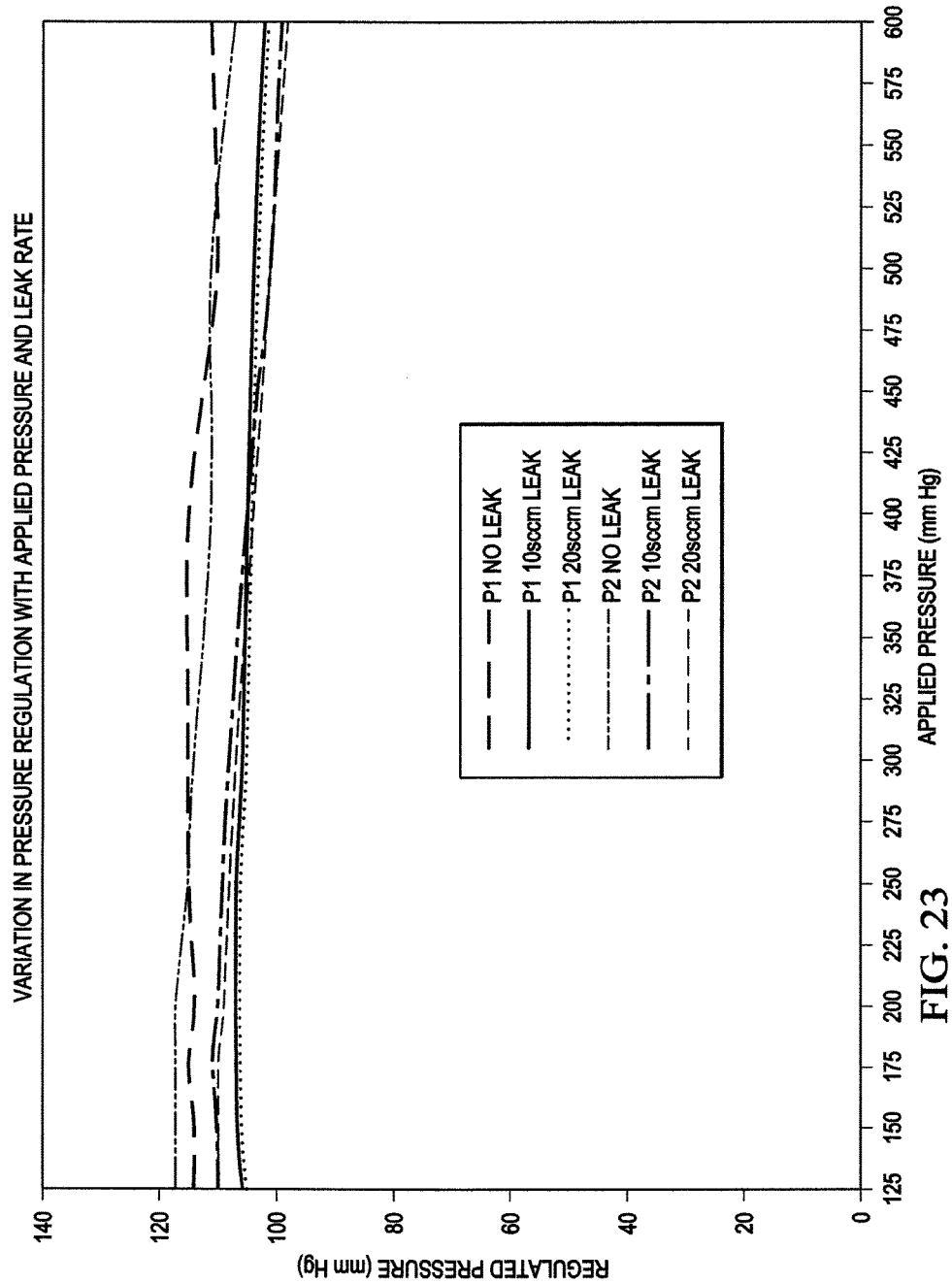
FIG. 23 is a graphical depiction of regulated pressure supplied by the reduced pressure treatment apparatus to a tissue site versus the applied pressure supplied to the reduced pressure treatment apparatus by an external source.

FIG. 23 is a graphical representation of a regulated pressure (i.e. the therapy pressure) supplied at the outlet port 227 compared to the reduced pressure (i.e. the applied pressure) applied to the valve assembly 400. The graphical representation of FIG. 23 is based upon testing of two exemplary reduced-pressure sources 211 that were supplied with reduced pressure from an external reduced-pressure source. As shown in FIG. 23, a first reduced-pressure source P1 and a second reduced-pressure source P2 were tested in three different scenarios. The reduced-pressure sources P1 and P2 are both examples of the reduced-pressure source 211. In the first scenario there was no leak at the tissue site. In the second scenario, there was a 10 standard cubic centimeter per minute ("sccm") leak at the tissue site. In the third scenario, there was a 20 sccm leak at the tissue site. The first reduced-pressure source P1 provided a therapy pressure of about 112 mm Hg with no leak at an applied pressure of 125 mm Hg and provided a therapy pressure of about 101 mm Hg with a 20 sccm leak at an applied pressure of about 600 mm Hg. The second reduced-pressure source P2 provided a therapy pressure of about 117 mm Hg with no leak at an applied pressure of 125 mm Hg and provided a therapy pressure of about 98 mm Hg with a 20 sccm leak at an applied pressure of about 600 mm Hg.

In another test, a 1 L/min (1000 sccm) leak was provided at the dressing. The therapy pressure provided dropped from about 122.3 mm Hg with no leak to about 98 mm Hg at 1 L/min leak. If the leak reached about 1 L/min, the alarm threshold was crossed, providing the audible alert that there may be a high flow through the reduced-pressure source 211. The audible alert may be present during dressing draw down, but as described above, the sound may be muted with the end cap 339. In additional testing, the reduced-pressure source 211 continued to effectively regulate therapy pressure until the leak reached a flow rate of 3 L/min (3000 sccm). At a leak flow rate of 3 L/min, the flow rate of the leak exceed the supply of reduced pressure at the valve assembly 400, causing the second barrel 219 to rise out of the first barrel 215. The rise of the second barrel 219 out of the first barrel 215 indicated that a pressure in the charging chamber 355 dropped below the level required to sustain therapy pressure at the outlet port 227.

In the various test cases, the reduced-pressure sources 211 were able to regulate pressure delivery to the outlet 227 within a range of about 10 mm Hg of a desired 125 mm Hg therapy pressure. In these test cases, the valve assembly 400 was supplied with reduced pressures ranging from about 125 mm Hg to about 600 mm Hg. In the exemplary test cases, as the flow of reduced pressure to the reduced-pressure source 211 was adjusted, the reduced-pressure source 211 continued to regulate pressure supplied to the tissue site.

If a patient no longer has access to hospital infrastructure, such as the wall-suction source, the reduced-pressure source 211 may be manually operated to continue supplying reduced pressure to a tissue site. A user may no longer have access to hospital infrastructure if the user is moved between facilities or if the user returns to a home environment, for example. In these examples, the external reduced-pressure source may be disconnected from the reduced-pressure source 211, and the valve 421 may close. In the event that reduced-pressure therapy is currently being supplied to a tissue site, closure of the valve 421 may maintain the charge of the charging chamber 355 if the external reduced-pressure source is disconnected. In the event that a leak develops in the dressing at the tissue site, the charge of the charging chamber 355 may be used to restore the therapy pressure at the dressing or tissue site. As the charge in the charging chamber 355 is used, the second barrel 219 may be forced out of the first barrel 215 by the piston spring 243, providing a visual cue to the user that there may be a leak at the tissue site or the dressing. If the second barrel 219 reaches the fully extended position of FIG. 11, the user may then manually operate the reduced-pressure source 211 as described above to continue reduced-pressure therapy. In this manner, the user may start therapy with the reduced-pressure source 211 in a hospital environment and may be able to be continue reduced-pressure therapy with the same device if the user is discharged to return home.

The systems and methods described herein may provide significant advantages, some of which have already been mentioned. For example, the manually-actuated pump may be fluidly connected in line between wall-suction and a standard 'Bemis' type collection canister, allowing the pump to provide regulated pressure to a tissue site through the canister, while the tissue site is being managed with a traditional VAC dressing. The manually-actuated pump may also have an enlarged charging chamber, providing a greater reservoir of reduced pressure. The manually-actuated pump may also provide visual and auditory indicators of undesired operation. For example, a large leak of a dressing can exceed the flow rate of the reduced pressure supplied to the valve assembly, causing the second barrel to rise and indicating a leak condition to the user or caregiver. In another example, a leak of the dressing may not exceed the flow rate of the reduced pressure supplied to the valve assembly; however, the alarm threshold may be crossed, indicating to the user or caregiver that there may be a leak at the dressing.

The manually-actuated pump also allows one device to be suited for multiple care settings. For example, the manually-actuated pump allows a patient in the acute environment to become mobile for periods of time with no loss of therapy and no need to carry around a large therapy device. Using the manually-actuated pump to control the therapy pressure provided by a wall-suction source or electrically operated pump may also be safer for the patient as excessive pressure outside the specified range can cause a manually-actuated pump to close and shut off therapy. In these scenarios, the dressing can still absorb fluids. The manually-actuated pump may be useful for initial dressing application and helpful in achieving an initial seal. Once the dressing is applied and an initial seal is achieved, the user may go home with a portable device that is operable without the wall-suction source.

Some patients may be unable to physically operate the manually-actuated pump. These patients may be provided with a secondary dumb pump unit, a pump without additional controls or sensors for example, which can charge the manually-actuated pump through the valve assembly periodically. The valve assembly of the manually-actuated pump may also vent the charging chamber through the valve assembly as the manually-actuated pump is manually charged rather than past the valve skirt as in other manually-actuated pumps. Venting through the valve assembly may reduce the noise associated with operation of the manually-actuated pump.

It should be apparent from the foregoing that an invention having significant advantages has been provided. While the invention is shown in only a few of its forms, it is not just limited but is susceptible to various changes and modifications without departing from the spirit thereof.

We claim:

1. A manually-actuated pump for applying reduced-pressure therapy, comprising:
   a charging chamber having a closed end;
   a regulated chamber;
   a regulator passage between the charging chamber and the regulated chamber;
   a valve body adapted to control fluid communication through the regulator passage;
   a regulator spring engaged with the valve body to bias the valve body against a differential between a pressure in the regulated chamber and an ambient pressure;
   an outlet port coupled to the regulated chamber; and
   a valve assembly coupled to the charging chamber to permit fluid flow through the closed end of the charging chamber.

2. The manually-actuated pump of claim 1, wherein the valve assembly permits fluid flow from the charging chamber through the valve assembly in response to a supplied pressure that is less than the pressure in the charging chamber.

3. The manually-actuated pump of claim 2, wherein the supplied pressure is in a range of about −125 mm Hg to about −600 mm Hg.

4. The manually-actuated pump of claim 2, wherein the supplied pressure is about −125 mm Hg.

5. The manually-actuated pump of claim 2, wherein the supplied pressure is about −600 mm Hg.

6. The manually-actuated pump of claim 1, wherein the valve assembly comprises a duckbill valve.

7. The manually-actuated pump of claim 1, wherein the valve assembly comprises a butterfly valve.

8. The manually-actuated pump of claim 1, wherein the valve assembly comprises an umbrella valve.

9. The manually-actuated pump of claim 1, wherein the valve assembly comprises a sprung-ball valve.

10. The manually-actuated pump of claim 1, wherein the closed end has an aperture and the valve assembly comprises:
    a valve adapter disposed within the aperture and having a chamber flange and a barrel flange, the chamber flange disposed within the charging chamber and the barrel flange disposed adjacent the closed end and external to the charging chamber;
    a high pressure adapter coupled to the valve adapter and having a nipple;
    a valve having a connector and a flattened end, the connector coupled to the nipple of the high pressure adapter; and
    wherein the flattened end has a slit configured to permit fluid flow out of the charging chamber.

11. The manually-actuated pump of claim 1, wherein the valve assembly is adapted to fluidly coupled to an external reduced-pressure source.

12. A reduced pressure treatment apparatus comprising:
    a piston chamber having a closed end;
    a piston disposed within the piston chamber and being movable between an extended position and a compressed position;
    a charging chamber disposed between the piston and the closed end;
    a biasing member adapted to bias the piston toward the extended position;
    a valve member adapted to allow fluid to exit the charging chamber as the piston moves toward the compressed position and to prevent fluid from entering the charging chamber as the piston moves toward the extended position;
    a regulated chamber;
    a passage between the regulated chamber and the charging chamber;
    a regulator member to regulate fluid communication through the passage between the charging chamber and the regulated chamber; and
    a valve assembly coupled to the charging chamber to permit fluid flow through the closed end of the charging chamber.

13. The reduced pressure treatment apparatus of claim 12, wherein the valve assembly permits fluid flow from the charging chamber through the valve assembly in response to a supplied pressure that is less than the pressure in the charging chamber.

14. The reduced pressure treatment apparatus of claim 13, wherein the supplied pressure is in a range of about −125 mm Hg to about −600 mm Hg.

15. The reduced pressure treatment apparatus of claim 13, wherein the supplied pressure is about −125 mm Hg.

16. The reduced pressure treatment apparatus of claim 13, wherein the supplied pressure is about −600 mm Hg.

17. The reduced pressure treatment apparatus of claim 12, wherein the valve assembly comprises a duckbill valve.

18. The reduced pressure treatment apparatus of claim 12, wherein the valve assembly comprises a butterfly valve.

19. The reduced pressure treatment apparatus of claim 12, wherein the valve assembly comprises an umbrella valve.

20. The reduced pressure treatment apparatus of claim 12, wherein the valve assembly comprises a sprung-ball valve.

21. The reduced pressure treatment apparatus of claim 12, wherein the closed end has an aperture and the valve assembly comprises:
   a valve adapter disposed within the aperture and having a chamber flange and a barrel flange, the chamber flange disposed within the charging chamber and the barrel flange disposed adjacent the closed end and external to the charging chamber;
   a high pressure adapter coupled to the valve adapter and having a nipple;
   a valve having a connector and a flattened end, the connector coupled to the nipple of the high pressure adapter; and
   wherein the flattened end has a slit configured to permit fluid flow out of the charging chamber.

22. The reduced pressure treatment apparatus of claim 12, wherein the valve assembly is adapted to fluidly coupled to an external reduced-pressure source.

23. A reduced pressure treatment system comprising:
   a manifold adapted to be positioned at a tissue site;
   a regulated chamber having an output port in fluid communication with the manifold and adapted to deliver a desired therapy pressure to the tissue site;
   a charging chamber having a closed end and adapted to store a charging pressure that is less than the desired therapy pressure;
   a passage adapted to provide fluid communication between the regulated chamber and the charging chamber; and
   a valve body operably associated with the passage to substantially reduce fluid communication through the passage if a pressure in the regulated chamber is less than or equal to the desired therapy pressure and to allow fluid communication through the passage if the pressure in the regulated chamber exceeds the desired therapy pressure;
   a valve assembly coupled to the closed end of the charging chamber and adapted to be fluidly coupled to an external reduced-pressure source to permit fluid flow out of the charging chamber in response to a supplied pressure provided by the external reduced-pressure source that is less than the pressure in the charging chamber.

24. The system of claim 23, wherein the supplied pressure is in a range of about −125 mm Hg to about −600 mm Hg.

25. The system of claim 23, wherein the supplied pressure is about −125 mm Hg.

26. The system of claim 23, wherein the supplied pressure is about −600 mm Hg.

27. The system of claim 23, wherein the valve assembly comprises a duckbill valve.

28. The system of claim 23, wherein the valve assembly comprises a butterfly valve.

29. The system of claim 23, wherein the valve assembly comprises an umbrella valve.

30. The system of claim 23, wherein the valve assembly comprises a sprung-ball valve.

31. The system of claim 23, wherein the closed end has an aperture and the valve assembly comprises:
   a valve adapter disposed within the aperture and having a chamber flange and a barrel flange, the chamber flange disposed within the charging chamber and the barrel flange disposed adjacent the closed end and external to the charging chamber;
   a high pressure adapter coupled to the valve adapter and having a nipple;
   a valve having a connector and a flattened end, the connector coupled to the nipple of the high pressure adapter; and
   wherein the flattened end has a slit configured to permit fluid flow out of the charging chamber.

32. The system of claim 23, wherein the external reduced-pressure source is a wall-suction source.

33. The system of claim 23, wherein the external reduced-pressure source is an electrically driven pump.

34. A method of providing reduced pressure treatment to a tissue site, the method comprising:
   storing a charging pressure within a charging chamber with an external reduced-pressure source;
   delivering a desired therapy pressure from a regulated chamber having an outlet port to the tissue site; and
   if a pressure within the regulated chamber exceeds the desired therapy pressure, reducing the pressure within the regulated chamber by allowing fluid communication between the charging chamber and the outlet port of the regulated chamber.

35. The method of claim 34 wherein the external reduced-pressure source is a wall-suction source.

36. The method of claim 34 wherein the external reduced-pressure source is an electrically driven pump.

37. The method of claim 34 wherein storing a charging pressure comprises coupling the external reduced-pressure source to a closed end of the charging chamber and opening a valve assembly to allow the flow of reduced pressure.

\* \* \* \* \*